(12) United States Patent
Dowling et al.

(10) Patent No.: US 7,303,300 B2
(45) Date of Patent: Dec. 4, 2007

(54) METHODS AND SYSTEMS FOR ILLUMINATING HOUSEHOLD PRODUCTS

(75) Inventors: Kevin J. Dowling, Westford, MA (US); Charles H. Cella, Pembroke, MA (US); Josh Strauss, Evanston, IL (US); Michael K. Blackwell, Milton, MA (US)

(73) Assignee: Color Kinetics Incorporated, Boston, MA (US)

( * ) Notice: Subject to any disclaimer, the term of this patent is extended or adjusted under 35 U.S.C. 154(b) by 295 days.

(21) Appl. No.: 10/656,807

(22) Filed: Sep. 5, 2003

(65) Prior Publication Data

US 2005/0036300 A1 Feb. 17, 2005
US 2006/0262516 A9 Nov. 23, 2006

Related U.S. Application Data

(63) Continuation-in-part of application No. 10/325,635, filed on Dec. 19, 2002, and a continuation-in-part of application No. 10/245,786, filed on Sep. 17, 2002, now Pat. No. 6,965,205, which is a continuation-in-part of application No. 09/716,819, filed on Nov. 20, 2000, now Pat. No. 7,014,336.

(60) Provisional application No. 60/452,767, filed on Mar. 7, 2003, provisional application No. 60/408,309, filed on Sep. 5, 2002, provisional application No. 60/353,569, filed on Feb. 1, 2002, provisional application No. 60/235,678, filed on Sep. 27, 2000.

(51) Int. Cl.
*F21V 33/00* (2006.01)

(52) U.S. Cl. .................................... 362/101; 362/231
(58) Field of Classification Search .................. 362/96, 362/101, 231, 249, 800, 217; 315/297, 312
See application file for complete search history.

(56) References Cited

U.S. PATENT DOCUMENTS

| 1,389,132 | A | * | 8/1921 | Galavan ..................... 362/101 |
| 2,909,097 | A | | 10/1959 | Alden et al. |
| 3,318,185 | A | | 5/1967 | Kott |
| 3,561,719 | A | | 2/1971 | Grindle |
| 3,586,936 | A | | 6/1971 | McLeroy |
| 3,595,991 | A | | 7/1971 | Diller |
| 3,601,621 | A | | 8/1971 | Ritchie |
| 3,643,088 | A | | 2/1972 | Osteen et al. |
| 3,696,393 | A | | 10/1972 | McDonald |

(Continued)

FOREIGN PATENT DOCUMENTS

AU 6 267 9 12/1996

(Continued)

OTHER PUBLICATIONS

"LM117-LM317A-LM317 3-Terminal Adjustable Regulator", National Semiconductor Corporation, May 1997, pp. 1-20.

(Continued)

*Primary Examiner*—John Anthony Ward
(74) *Attorney, Agent, or Firm*—Wolf, Greenfield & Sacks, P.C.

(57) ABSTRACT

Methods and systems are provided herein for illuminating a variety of household products and other items using color-controlled illumination systems that include lights under the control of processors.

39 Claims, 15 Drawing Sheets

U.S. PATENT DOCUMENTS

| | | |
|---|---|---|
| 3,740,570 A | 6/1973 | Kaelin et al. |
| 3,746,918 A | 7/1973 | Drucker et al. |
| 3,760,174 A | 9/1973 | Boenning et al. |
| 3,818,216 A | 6/1974 | Larraburu |
| 3,832,503 A | 8/1974 | Crane |
| 3,858,086 A | 12/1974 | Anderson et al. |
| 3,909,670 A | 9/1975 | Wakamatsu et al. |
| 3,924,120 A | 12/1975 | Cox, III |
| 3,958,885 A | 5/1976 | Stockinger et al. |
| 3,974,637 A | 8/1976 | Bergey et al. |
| 4,001,571 A | 1/1977 | Martin |
| 4,054,814 A | 10/1977 | Fegley et al. |
| 4,070,568 A | 1/1978 | Gala |
| 4,082,395 A | 4/1978 | Donato et al. |
| 4,096,349 A | 6/1978 | Donato |
| 4,241,295 A | 12/1980 | Williams, Jr. |
| 4,271,408 A | 6/1981 | Teshima et al. |
| 4,272,689 A | 6/1981 | Crosby et al. |
| 4,273,999 A | 6/1981 | Pierpoint |
| 4,298,869 A | 11/1981 | Okuno |
| 4,329,625 A | 5/1982 | Nishizawa et al. |
| 4,339,788 A | 7/1982 | White et al. |
| 4,342,947 A | 8/1982 | Bloyd |
| 4,360,804 A | 11/1982 | Okura |
| 4,367,464 A | 1/1983 | Kurahashi et al. |
| 4,388,567 A | 6/1983 | Yamazaki et al. |
| 4,388,589 A | 6/1983 | Molldrem, Jr. |
| 4,392,187 A | 7/1983 | Bornhorst |
| 4,394,600 A | 7/1983 | Flannagan |
| 4,420,711 A | 12/1983 | Takahashi et al. |
| 4,455,562 A | 6/1984 | Dolan et al. |
| 4,500,796 A | 2/1985 | Quin |
| 4,515,295 A * | 5/1985 | Dougherty .................. 222/113 |
| 4,559,480 A | 12/1985 | Nobs |
| 4,581,612 A | 4/1986 | Jones |
| 4,581,655 A | 4/1986 | Ide et al. |
| 4,597,033 A | 6/1986 | Meggs et al. |
| 4,612,720 A | 9/1986 | Manners-Smith et al. |
| 4,622,881 A | 11/1986 | Rand |
| 4,625,152 A | 11/1986 | Nakai |
| 4,635,052 A | 1/1987 | Aoike et al. |
| 4,644,342 A | 2/1987 | Abbas |
| 4,647,217 A | 3/1987 | Havel |
| 4,654,629 A | 3/1987 | Bezos et al. |
| 4,656,398 A | 4/1987 | Michael et al. |
| 4,668,895 A | 5/1987 | Schneiter |
| 4,675,575 A | 6/1987 | Smith et al. |
| 4,682,079 A | 7/1987 | Sanders et al. |
| 4,686,425 A | 8/1987 | Havel |
| 4,687,340 A | 8/1987 | Havel |
| 4,688,154 A | 8/1987 | Nilssen |
| 4,688,869 A | 8/1987 | Kelly |
| 4,695,769 A | 9/1987 | Schweickardt |
| 4,701,669 A | 10/1987 | Head et al. |
| 4,705,406 A | 11/1987 | Havel |
| 4,707,141 A | 11/1987 | Havel |
| 4,720,709 A | 1/1988 | Imanura et al. |
| 4,727,289 A | 2/1988 | Uchida |
| 4,740,882 A | 4/1988 | Miller |
| 4,753,148 A | 6/1988 | Johnson |
| 4,771,274 A | 9/1988 | Havel |
| 4,780,621 A | 10/1988 | Bartleucci et al. |
| 4,782,336 A | 11/1988 | Bailey |
| 4,794,383 A | 12/1988 | Havel |
| 4,818,072 A | 4/1989 | Mohebban |
| 4,824,269 A | 4/1989 | Havel |
| 4,833,542 A | 5/1989 | Hara et al. |
| 4,837,565 A | 6/1989 | White |
| 4,843,627 A | 6/1989 | Stebbins |
| 4,845,481 A | 7/1989 | Havel |
| 4,845,745 A | 7/1989 | Havel |
| 4,857,801 A | 8/1989 | Farrell |
| 4,858,088 A | 8/1989 | Agabekov |
| 4,863,223 A | 9/1989 | Weissenbach et al. |
| 4,870,325 A | 9/1989 | Kazar |
| 4,874,320 A | 10/1989 | Freed et al. |
| 4,887,074 A | 12/1989 | Simon et al. |
| 4,922,154 A | 5/1990 | Cacoub |
| 4,934,852 A | 6/1990 | Havel |
| 4,962,687 A | 10/1990 | Belliveau et al. |
| 4,965,561 A | 10/1990 | Havel |
| 4,973,835 A | 11/1990 | Kurosu et al. |
| 4,979,081 A | 12/1990 | Leach et al. |
| 4,980,806 A | 12/1990 | Taylor et al. |
| 4,992,704 A | 2/1991 | Stinson |
| 5,003,227 A | 3/1991 | Nilssen |
| 5,008,595 A | 4/1991 | Kazar |
| 5,008,788 A | 4/1991 | Palinkas |
| 5,010,459 A | 4/1991 | Taylor et al. |
| 5,027,262 A | 6/1991 | Freed |
| 5,034,807 A | 7/1991 | Von Kohorn |
| 5,036,248 A | 7/1991 | McEwan et al. |
| 5,038,255 A | 8/1991 | Nishihashi et al. |
| 5,072,216 A | 12/1991 | Grange |
| 5,078,039 A | 1/1992 | Tulk et al. |
| 5,083,063 A | 1/1992 | Brooks |
| 5,089,748 A | 2/1992 | Ihms |
| 5,122,733 A | 6/1992 | Havel |
| 5,126,634 A | 6/1992 | Johnson |
| 5,128,595 A | 7/1992 | Hara |
| 5,130,909 A | 7/1992 | Gross |
| 5,134,387 A | 7/1992 | Smith et al. |
| 5,142,199 A | 8/1992 | Elwell |
| 5,154,641 A | 10/1992 | McLaughlin |
| 5,161,879 A | 11/1992 | McDermott |
| 5,164,715 A | 11/1992 | Kashiwabara et al. |
| 5,184,114 A | 2/1993 | Brown |
| 5,194,854 A | 3/1993 | Havel |
| 5,209,560 A | 5/1993 | Taylor et al. |
| 5,225,765 A | 7/1993 | Callahan et al. |
| 5,226,723 A | 7/1993 | Chen |
| 5,254,910 A | 10/1993 | Yang |
| 5,256,948 A | 10/1993 | Boldin et al. |
| 5,278,542 A | 1/1994 | Smith et al. |
| 5,282,121 A | 1/1994 | Bornhorst et al. |
| 5,283,517 A | 2/1994 | Havel |
| 5,287,352 A | 2/1994 | Jackson et al. |
| 5,294,865 A | 3/1994 | Haraden |
| 5,298,871 A | 3/1994 | Shimohara |
| 5,301,090 A | 4/1994 | Hed |
| 5,307,295 A | 4/1994 | Taylor et al. |
| 5,575,554 A | 11/1996 | Guritz |
| 5,592,051 A | 1/1997 | Korkala |
| 5,607,227 A | 3/1997 | Yasumoto et al. |
| 5,614,788 A | 3/1997 | Mullins et al. |
| 5,621,282 A | 4/1997 | Haskell |
| 5,621,603 A | 4/1997 | Adamec et al. |
| 5,633,629 A | 5/1997 | Hockstein |
| 5,634,711 A | 6/1997 | Kennedy et al. |
| 5,640,061 A | 6/1997 | Bornhorst et al. |
| 5,642,129 A | 6/1997 | Zavracky et al. |
| 5,653,529 A | 8/1997 | Spocharski |
| 5,656,935 A | 8/1997 | Havel |
| 5,673,059 A | 9/1997 | Zavracky et al. |
| 5,684,309 A | 11/1997 | McIntosh et al. |
| 5,688,042 A | 11/1997 | Madadi et al. |
| 5,701,058 A | 12/1997 | Roth |
| 5,712,650 A | 1/1998 | Barlow |
| 5,721,471 A | 2/1998 | Begemann et al. |
| 5,734,590 A | 3/1998 | Tebbe |
| 5,751,118 A | 5/1998 | Mortimer |
| 5,752,766 A | 5/1998 | Bailey et al. |
| 5,769,527 A | 6/1998 | Taylor et al. |
| 5,784,006 A | 7/1998 | Hockstein |

| | | | | | | |
|---|---|---|---|---|---|---|
| 5,790,329 | A | 8/1998 | Klaus et al. | 6,357,893 | B1 | 3/2002 | Belliveau |
| 5,796,376 | A | 8/1998 | Banks | 6,361,186 | B1 | 3/2002 | Slayden |
| 5,803,579 | A | 9/1998 | Turnbull et al. | 6,369,525 | B1 | 4/2002 | Chang et al. |
| 5,808,689 | A | 9/1998 | Small | 6,371,637 | B1 | 4/2002 | Atchinson et al. |
| 5,812,105 | A | 9/1998 | Van de Ven | 6,379,209 | B1 | 4/2002 | Tucker |
| 5,821,695 | A | 10/1998 | Vilanilam et al. | 6,445,139 | B1 | 9/2002 | Marshall et al. |
| 5,836,676 | A | 11/1998 | Ando et al. | 6,448,550 | B1 | 9/2002 | Nishimura |
| 5,848,837 | A | 12/1998 | Gustafson | 6,459,919 | B1 | 10/2002 | Lys et al. |
| 5,850,126 | A | 12/1998 | Kanbar | 6,476,779 | B1 | 11/2002 | Yano et al. |
| 5,851,063 | A | 12/1998 | Doughty et al. | 6,495,964 | B1 | 12/2002 | Muthu et al. |
| 5,852,658 | A | 12/1998 | Knight et al. | 6,528,954 | B1 | 3/2003 | Lys et al. |
| 5,854,542 | A | 12/1998 | Forbes | 6,540,373 | B2 | 4/2003 | Bailey |
| RE36,030 | E | 1/1999 | Nadeau | 6,543,164 | B1 | 4/2003 | Sperl et al. |
| 5,859,508 | A | 1/1999 | Ge et al. | 6,550,952 | B1 | 4/2003 | Hulse et al. |
| 5,896,010 | A | 4/1999 | Mikolajczak et al. | 6,551,282 | B1 | 4/2003 | Exline et al. |
| 5,900,850 | A | 5/1999 | Bailey et al. | 6,558,021 | B2 | 5/2003 | Wu et al. |
| 5,907,742 | A | 5/1999 | Johnson et al. | 6,561,690 | B2 | 5/2003 | Balestriero et al. |
| 5,912,653 | A | 6/1999 | Fitch | 6,566,824 | B2 | 5/2003 | Panagotacos et al. |
| 5,924,784 | A | 7/1999 | Chliwnyj et al. | 6,568,834 | B1 | 5/2003 | Scianna |
| 5,927,845 | A | 7/1999 | Gustafson et al. | 6,577,080 | B2 | 6/2003 | Lys et al. |
| 5,946,209 | A | 8/1999 | Eckel et al. | 6,582,103 | B1 | 6/2003 | Popovich et al. |
| 5,949,581 | A | 9/1999 | Kurtenbach et al. | 6,592,238 | B2 | 7/2003 | Cleaver et al. |
| 5,952,680 | A | 9/1999 | Strite | 6,596,977 | B2 | 7/2003 | Muthu et al. |
| 5,959,547 | A | 9/1999 | Tubel et al. | 6,603,243 | B2 | 8/2003 | Parkyn et al. |
| 5,961,201 | A | 10/1999 | Gismondi | 6,608,453 | B2 | 8/2003 | Morgan et al. |
| 5,963,185 | A | 10/1999 | Havel | 6,624,597 | B2 | 9/2003 | Dowling et al. |
| 5,974,553 | A | 10/1999 | Gandar | 6,636,003 | B2 | 10/2003 | Rahm et al. |
| 5,980,064 | A | 11/1999 | Metroyanis | 6,639,574 | B2 | 10/2003 | Scheibe |
| 6,008,783 | A | 12/1999 | Kitagawa et al. | 6,642,666 | B1 | 11/2003 | St. Germain |
| 6,016,038 | A | 1/2000 | Mueller et al. | 6,680,579 | B2 | 1/2004 | Allen et al. |
| 6,018,237 | A | 1/2000 | Havel | 6,683,423 | B2 | 1/2004 | Cunningham |
| 6,020,825 | A | 2/2000 | Chansky et al. | 6,690,341 | B2 | 2/2004 | Tokimoto et al. |
| 6,025,550 | A | 2/2000 | Kato | 6,693,385 | B2 | 2/2004 | Koyama |
| 6,028,582 | A | 2/2000 | Drew et al. | 6,704,989 | B1 | 3/2004 | Lutz et al. |
| 6,031,343 | A | 2/2000 | Recknagel et al. | 6,707,389 | B2 | 3/2004 | Pederson |
| 6,056,420 | A | 5/2000 | Wilson et al. | 6,717,376 | B2 | 4/2004 | Lys et al. |
| 6,068,383 | A | 5/2000 | Robertson et al. | 6,720,745 | B2 | 4/2004 | Mueller et al. |
| 6,069,595 | A | 5/2000 | Tokimoto | 6,749,310 | B2 | 6/2004 | Pohlert |
| 6,069,597 | A | 5/2000 | Hansen | 6,781,329 | B2 * | 8/2004 | Mueller et al. ............. 315/297 |
| 6,072,280 | A | 6/2000 | Allen | 2001/0033488 | A1 | 10/2001 | Chliwnyj et al. |
| 6,074,074 | A | 6/2000 | Marcus | 2002/0038157 | A1 | 3/2002 | Dowling et al. |
| 6,092,915 | A | 7/2000 | Rensch | 2002/0044066 | A1 | 4/2002 | Dowling et al. |
| 6,095,661 | A | 8/2000 | Lebens et al. | 2002/0047569 | A1 | 4/2002 | Dowling et al. |
| 6,097,352 | A | 8/2000 | Zavracky et al. | 2002/0047624 | A1 | 4/2002 | Stam et al. |
| 6,104,414 | A | 8/2000 | Odryna et al. | 2002/0048169 | A1 | 4/2002 | Dowling et al. |
| 6,127,783 | A | 10/2000 | Pashley et al. | 2002/0057061 | A1 | 5/2002 | Mueller et al. |
| 6,132,072 | A | 10/2000 | Turnbull et al. | 2002/0060526 | A1 | 5/2002 | Timmermans et al. |
| 6,135,604 | A | 10/2000 | Lin | 2002/0070688 | A1 | 6/2002 | Dowling et al. |
| 6,150,774 | A | 11/2000 | Mueller et al. | 2002/0074559 | A1 | 6/2002 | Dowling et al. |
| 6,158,882 | A | 12/2000 | Bischoff, Jr. | 2002/0078221 | A1 | 6/2002 | Blackwell et al. |
| 6,166,496 | A | 12/2000 | Lys et al. | 2002/0101197 | A1 | 8/2002 | Lys et al. |
| 6,175,342 | B1 | 1/2001 | Nicholson et al. | 2002/0126064 | A1 | 9/2002 | Yen |
| 6,177,761 | B1 | 1/2001 | Pelka et al. | 2002/0130627 | A1 | 9/2002 | Morgan et al. |
| 6,181,126 | B1 | 1/2001 | Havel | 2002/0145394 | A1 | 10/2002 | Morgan et al. |
| 6,183,086 | B1 | 2/2001 | Neubert | 2002/0145869 | A1 | 10/2002 | Dowling |
| 6,183,104 | B1 | 2/2001 | Ferrara | 2002/0152045 | A1 | 10/2002 | Dowling et al. |
| 6,184,628 | B1 | 2/2001 | Ruthenberg | 2002/0153851 | A1 | 10/2002 | Morgan et al. |
| 6,196,471 | B1 | 3/2001 | Ruthenberg | 2002/0158583 | A1 | 10/2002 | Lys et al. |
| 6,211,626 | B1 | 4/2001 | Lys et al. | 2002/0163316 | A1 | 11/2002 | Dowling et al. |
| 6,215,409 | B1 | 4/2001 | Blach | 2002/0171365 | A1 | 11/2002 | Morgan et al. |
| 6,237,290 | B1 | 5/2001 | Tokomoto et al. | 2002/0171377 | A1 | 11/2002 | Mueller et al. |
| 6,250,774 | B1 | 6/2001 | Begemann et al. | 2002/0171378 | A1 | 11/2002 | Morgan et al. |
| 6,252,358 | B1 | 6/2001 | Xydis et al. | 2002/0176259 | A1 | 11/2002 | Ducharme |
| 6,273,338 | B1 | 8/2001 | White | 2002/0195975 | A1 | 12/2002 | Dowling et al. |
| 6,283,612 | B1 | 9/2001 | Hunter | 2003/0011538 | A1 | 1/2003 | Lys et al. |
| 6,292,901 | B1 | 9/2001 | Lys et al. | 2003/0028260 | A1 | 2/2003 | Blackwell |
| 6,310,590 | B1 | 10/2001 | Havel | 2003/0057884 | A1 | 3/2003 | Dowling et al. |
| 6,314,669 | B1 | 11/2001 | Tucker | 2003/0057886 | A1 | 3/2003 | Lys et al. |
| 6,323,832 | B1 | 11/2001 | Nishizawa et al. | 2003/0057887 | A1 | 3/2003 | Dowling et al. |
| 6,329,764 | B1 | 12/2001 | van de Ven | 2003/0057890 | A1 | 3/2003 | Lys et al. |
| 6,330,111 | B1 | 12/2001 | Myers | 2003/0076281 | A1 | 4/2003 | Morgan et al. |
| 6,331,915 | B1 | 12/2001 | Myers | 2003/0100837 | A1 | 5/2003 | Lys et al. |
| 6,340,868 | B1 | 1/2002 | Lys et al. | 2003/0107887 | A1 | 6/2003 | Eberl |

| | | | |
|---|---|---|---|
| 2003/0133292 A1 | 7/2003 | Mueller et al. | |
| 2003/0137258 A1 | 7/2003 | Piepgras et al. | |
| 2003/0189412 A1 | 10/2003 | Cunningham | |
| 2003/0198061 A1 | 10/2003 | Chambers et al. | |
| 2003/0222587 A1 | 12/2003 | Dowling et al. | |
| 2004/0032226 A1 | 2/2004 | Lys | |
| 2004/0036006 A1 | 2/2004 | Dowling | |
| 2004/0052076 A1 | 3/2004 | Mueller et al. | |
| 2004/0066652 A1 | 4/2004 | Hong | |
| 2004/0090787 A1 | 5/2004 | Dowling et al. | |
| 2004/0105261 A1 | 6/2004 | Ducharme et al. | |
| 2004/0130909 A1 | 7/2004 | Mueller et al. | |
| 2005/0128743 A1 | 6/2005 | Chuey et al. | |

FOREIGN PATENT DOCUMENTS

| | | |
|---|---|---|
| CA | 2 178 432 | 12/1996 |
| CA | 2 134 848 | 11/1998 |
| DE | 02315709 | 10/1974 |
| DE | 0205307 | 12/1983 |
| DE | 03438154 A1 | 4/1986 |
| DE | 3837313 | 5/1989 |
| DE | 3805998 | 9/1989 |
| DE | 3925767 A1 | 4/1990 |
| DE | 8902905 | 5/1990 |
| DE | 3917101 | 11/1990 |
| DE | 3916875 | 12/1990 |
| DE | 4041338 | 7/1992 |
| DE | 4130576 C1 | 3/1993 |
| DE | 9414688 U1 | 2/1995 |
| DE | 9414689 | 2/1995 |
| DE | 4419006 A1 | 12/1995 |
| DE | 29607270 U1 | 8/1996 |
| DE | 19525987 | 10/1996 |
| DE | 29620583 U1 | 3/1997 |
| DE | 19651140 A1 | 6/1997 |
| DE | 19602891 A1 | 7/1997 |
| EP | 0482680 A1 | 4/1992 |
| EP | 0495305 A2 | 7/1992 |
| EP | 0567280 B1 | 10/1993 |
| EP | 0534710 B1 | 1/1996 |
| EP | 0734082 A2 | 9/1996 |
| EP | 0752632 A2 | 1/1997 |
| EP | 0752632 A3 | 8/1997 |
| EP | 0823812 A2 | 2/1998 |
| EP | 0935234 A1 | 8/1999 |
| EP | 0942631 A2 | 9/1999 |
| EP | 1020352 A2 | 7/2000 |
| EP | 1113215 A2 | 7/2001 |
| EP | 1162400 A2 | 12/2001 |
| FR | 2 640 791 | 6/1990 |
| FR | 88 17359 | 12/1998 |
| GB | 2045098 A | 10/1980 |
| GB | 2131589 A | 11/1982 |
| GB | 2135536 A | 8/1984 |
| GB | 2176042 A | 12/1986 |
| GB | 2210720 A | 6/1989 |
| JP | 2247688 | 10/1990 |
| JP | 03045166 | 2/1991 |
| JP | 06043830 | 2/1994 |
| JP | 7-39120 | 7/1995 |
| JP | 8-106264 | 4/1996 |
| JP | 8-007611 | 12/1996 |
| JP | 9 320766 | 12/1997 |
| KR | 1019910009812 | 11/1991 |
| WO | WO 89/05086 | 6/1989 |
| WO | WO 94/18809 | 8/1994 |
| WO | WO 95/13498 | 5/1995 |
| WO | WO 96/41098 | 12/1996 |
| WO | WO 99/06759 | 2/1999 |
| WO | WO 99/30537 A1 | 6/1999 |
| WO | WO 00/14705 | 3/2000 |
| WO | WO 01/73818 A1 | 10/2001 |
| WO | WO 02-061328 A1 | 8/2002 |

OTHER PUBLICATIONS

"DS96177 RS-485-RS-422 Differential Bus Repeater", National Semiconductor Corporation, Feb. 1996, pp. 1-8.

"DS2003-DA9667-DS2004 High Current—Voltage Darlington Drivers", National Semiconductor Corporation, Dec. 1995, pp. 1-8.

"LM140A-LM140-LM340A-LM7800C Series 3—Terminal Positive Regulators", National Semiconductor Corporation, Jan. 1995, pp. 1-14.

High End Systems, Inc., Trackspot User Manual, Aug. 1997, Excerpts (Cover, Title page, pp. ii through iii and 2-13 through 2-14).

Artistic License, AL4000 DMX512 Processors, Revision 3.4, Jun. 2000, Excerpts (Cover, pp. 7,92 through 102).

Artistic License, Miscellaneous Drawings (3 sheets) Jan. 12, 1995.

Artistic License, Miscellaneous Documents (2 sheets Feb. 1995 and Apr. 1996).

Newnes's Dictionary of Electronics, Fourth Edition, S.W. Amos, et al., Preface to First Edition, pp. 278-279.

"http:--www.luminus.cx-projects-chaser", (Nov. 13, 2000), pp. 1-16.

Hewlett Packard Components, "Solid State Display and Optoelectronics Designer's Catalog," pp. 30-43, Jul. 1973.

INTEC Research, TRACKSPOT, http:--www.intec-research.com-trackspot.htm, pp. 1-4, Apr. 24, 2003.

SHARP, Optoelectronics Data Book, pp. 1096-1097, 1994-1995.

About DMX-512 Lighting Protocol—Pangolin Laser Systems, pp. 1-4, Apr. 7, 2003.

Avitech Licht Design '89-90, pp. 1-4.

Dr. Ing, Ulrich Tietze, Dr. Ing, Christoph Schenk, pp. 566-569.

Case No. 6:02-cv-270-ORL-19JGG in the United States District Court, Middle District of Florida, Orlando Division, Plaintiff's Amended Verified Complaint.

Case No. 6:02-cv-270-ORL-19JGG in the United States District Court, Middle District of Florida, Orlando Division, Defendant's Answer and Counterclaims.

Case No. 6:02-cv-270-ORL-19JGG in the United States District Court, Middle District of Florida, Orlando Division, Plaintiff's Answer to Counterclaims.

Case No. 6:02-cv-270-ORL-19JGG in the United States District Court, Middle District of Florida, Orlando Division, Plaintiff's Answers to Defendant's First Set of Interrogatories w-Exhibit 1.

Case No. 02 CV 11137MEL in the United States District Court, District of Massachusetts, Plaintiff's Complaint and Jury Demand.

Case No. 02 CV 11137MEL in the United States District Court, District of Massachusetts, Defendant's Answer and Affirmative Defenses.

Furry, Kevin and Somerville, Chuck, Affidavit, LED effects, Feb. 22, 2002, pp. 24-29.

Putman, Peter H., "The Allure of LED," www.sromagazine.biz, Jun.-Jul. 2002, pp. 47-52.

Bremer, Darlene, "LED Advancements Increase Potential," www.ecmag.com, Apr. 2002, p. 115.

Longo, Linda, "LEDS Lead the Way," Home Lighting & Accessories, Jun. 2002, pp. 226-234.

iLight Technologies, "Explore the iLight Possibilities", http://www.ilight-tech.com, Sep. 7, 2004, 1 page.

iLight Technologies, "Curved or straight in white or color", http://www.ilight-tech.com/products.htm, Sep. 7, 2004, 1 page.

iLight Technologies, "Curved or straight in white or color",/ products_white.htm, Sep. 7, 2004, 1 page.

iLight Technologies, "Curved or straight in white or color",/ products_color.htm, Sep. 7, 2004, 1 page.

iLight Technologies, "Curved or straight in white or color",/ products_signs.htm, Sep. 7, 2004, 1 page.

* cited by examiner

METHODS AND SYSTEMS FOR ILLUMINATING HOUSEHOLD PRODUCTS

CROSS-REFERENCES TO RELATED APPLICATIONS

This application claims the benefit, under 35 U.S.C. §119(e), of the following U.S. Provisional Applications:

Ser. No. 60/408,309, filed Sep. 5, 2002, entitled "Methods and Systems for Illuminating Household Products;" and Ser. No. 60/452,767, filed Mar. 7, 2003, entitled "Light Emitting Diode Based Products."

This application also claims the benefit, under 35 U.S.C. §120, as a continuation-in-part (CIP) of the following U.S. Non-provisional Applications:

Ser. No. 10/245,786, filed Sep. 17, 2002 now U.S. Pat. No. 6,965,205, entitled "Light Emitting Diode Based Products," which in turn claims the benefit of U.S. provisional application Ser. No. 60/353,569 filed Feb. 1, 2002, entitled "LED Systems and Methods," both of which applications are hereby incorporated herein by reference, and Ser. No. 10/325,635, filed Dec. 19, 2002, entitled "Controlled Lighting Methods and Apparatus," which application also is hereby incorporated herein by reference, and which application is a continuation-in-part of Ser. No. 09/716,819, filed Nov. 20, 2000 now U.S. Pat. No. 7,014,336, entitled "Systems and Methods for Generating and Modulating Illumination Conditions," which in turn claims priority to U.S. provisional application Ser. No. 60/235,678, filed Sep. 27, 2000, entitled "Ultraviolet Light Emitting Diode Device."

BACKGROUND

Lighting elements often are used to illuminate a variety of consumer products, including wearable accessories, novelty items, or the like. Existing illuminated products, however, are generally only capable of exhibiting fixed illumination with one or more light sources. An existing wearable accessory, for example, might utilize a single white-light bulb as an illumination source, with the white-light shining through a transparent colored material. Such accessories only exhibit an illumination of a single type (a function of the color of the transparent material) or at best, by varying the intensity of the bulb output, a single-colored illumination with some range of controllable brightness. Other existing systems, to provide a wider range of colored illumination, may utilize a combination of differently colored bulbs. Such accessories, however, remain limited to a small number of different colored states.

SUMMARY

Applicants have generally recognized and appreciated that a variety of consumer products, including but not limited to household products and items, appliances and equipment associated with appliances, wearable accessories, novelty items, toys, games and the like may benefit from improved color illumination processing, and/or networking attributes. High-brightness LEDs, combined with a processor for control, can produce a variety of pleasing effects for display and illumination. Accordingly, one embodiment of the present invention relates to using high-brightness, processor-controlled LEDs in combination with diffuse materials to produce color-changing effects in connection with a variety of consumer products, including household items.

Methods and systems are provided for illuminating a fluid household product. The methods and systems include providing a container for the fluid household product, providing a light system in operative connection with the container, the light system comprising a light and a processor and being capable of producing illumination of a plurality of colors under control of the processor, and illuminating the fluid using the light system. The light system can illuminate a spray of fluid coming from the container. The light systems can illuminate fluids in transparent containers. The light systems can illuminate packaging for a household product.

A wide range of household products can benefit from methods and systems for color changing illumination.

Methods and systems are provided herein for illuminating packaging, including packaging for household products.

Methods and systems are provided herein for illuminating fluids, including liquids, visible gases and vapors, including all of those present in household products and household facilities, such as household water systems.

Methods and systems are provided herein for illuminating chemicals.

Methods and systems are provided herein for illuminating chemical household products.

Methods and systems are provided herein for illuminating products, including household products.

Methods and systems are provided herein for providing illumination for household products. Embodiments include a light system under the control of a processor for providing illumination of a selected color and disposing the illumination system in proximity to the household product to light a feature of the household product. In embodiments the product includes a container, such as a spray container, with the light system placed in the bottom of the container, the neck of the container, the interior of the container, the top of the container, or the nozzle of the container. The container may contain a fluid, such as water, ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, surface cleaner, and liquid wax. In embodiments the light system changes the color of the fluid in response to the processor. In embodiments the light system illuminates the spray of fluid coming from the container. In embodiments the spray produces a rainbow effect. In embodiments, the color of light changes in response to the processor. The container may be an aerosol can. Color changes may include different color temperatures of white light.

In embodiments, the household product may be a pencil, a pen, a fork, a knife, a spoon, a kitchen utensil, a whisk, a broom, a bottle, a glass, a mug, a coffee maker, a toothpaste tube, a dispenser, a shampoo bottle, a soap holder, a razor, an electric razor, a hair dryer, a picture frame, a marker, a jar, a makeup facility, a perfume dispenser, a brush, a lipstick, a candle or another household product.

In embodiments the processor changes light to indicate data related to the product, such as data about freshness or efficacy. The processor may respond to a network, including to addressable data. The processor may respond to a sensor.

Methods and systems may further include an optical facility for directing light, such as a lens, a mirror, a liquid lens, a spinning mirror, a fresnel lens, a convex lens, a concave lens, a fiber optic, and a light pipe.

Methods and systems are provided for insect control, including methods and systems for providing a light system with a plurality of LEDs and a processor for controlling a color of light from the LEDs; and providing an insect control facility in connection with the light system. The insect control facility can be a roach motel, a flypaper, a mosquito net, a tiki torch, a mosquito coil, a bug zapper, a deck light, a pool light or other facility. The processor can be used to control the light system to produce light of a selected frequency, including white light frequencies, such as to attract or repel selected insects. The insect control facility can be configured as a wand that contains the light system and that sprays insect spray.

Illumination methods and systems are provided herein for illuminating toilets, razors, brooms, animal collars, toothbrushes, candles, showerheads, and other household items.

Methods and systems are provided for illuminating an appliance, such as a faucet, a shower, a tub, a sink, an appliance, a refrigerator, an oven, a microwave, a counter, a drawer, a cabinet, a floor, a ceiling, a wall, a chair, a desk, a table, a washer, a dryer, a mixer, a blender, and a toaster. In embodiments, the light system responds to a sensor associated with the appliance, such as a heat sensor, such as to indicate that the appliance is hot.

Methods and systems are provided for packaging merchandise, including methods and systems for providing a light system with a plurality of LEDs and a processor for controlling a color of light from the LEDs and for disposing the light system in connection with packaging for an item of merchandise. In embodiments the packaging is a can, a container, a box, a package, or a shrinkwrap package. In embodiments, the merchandise is a household cleaner, a wax, a shampoo, a soap, a razor, a toothbrush, a light bulb or skin care product.

Methods and systems are provided for illuminating chemicals, including methods and systems for providing a light system with a plurality of LEDs and a processor for controlling a color of light from the LEDs and for lighting the chemical with the light system, wherein the light interacts with the chemical to create an effect. In embodiments the effect is generated by a luminescent facility of the chemical. In embodiments the effect is used to confirm that a chemical has been applied over a given surface. In embodiments, the chemical is an insect repellant, a deck sealer, a lotion, a medicine or a suntan lotion.

Methods and systems are provided for providing illumination and scent. Included are methods and systems for providing a light system with a plurality of LEDs and a processor for controlling a color of light from the LEDs and for providing a scent-producing facility for producing coordinated illumination and scent. In embodiments coordination is by a network. In embodiments the scent-producing facility is an air freshener. In embodiments the scent is correlated with illumination that reflects at least one of a similar aesthetic condition, an emotional state, an environmental condition, and a data item.

Methods and systems are provided for illuminating a fluid household product. The methods and systems include providing a container for the fluid household product, providing a light system in operative connection with the container, the light system comprising a light and a processor and being capable of producing illumination of a plurality of colors under control of the processor, and illuminating the fluid using the light system. In embodiments the light system illuminates a spray of fluid coming from the container. In embodiments the container is transparent and the light system illuminates fluid in the container. In embodiments the light system lights a package for the container.

The following patents and patent applications are hereby incorporated herein by reference:

U.S. Pat. No. 6,016,038, issued Jan. 18, 2000, entitled "Multicolored LED Lighting Method and Apparatus;"

U.S. Pat. No. 6,211,626, issued Apr. 3, 2001 to Lys et al, entitled "Components,"

U.S. Pat. No. 6,608,453, issued Aug. 19, 2003, entitled "Methods and Apparatus for Controlling Devices in a Networked Lighting System;"

U.S. Pat. No. 6,548,967, issued Apr. 15, 2003, entitled "Universal Lighting Network Methods and Systems;"

U.S. patent application Ser. No. 09/344,699, filed Jun. 25, 1999, entitled "Method for Software Driven Generation of Multiple Simultaneous High Speed Pulse Width Modulated Signals;"

U.S. patent application Ser. No. 09/805,368, filed Mar. 13, 2001, entitled "Light-Emitting Diode Based Products;"

U.S. patent application Ser. No. 09/716,819, filed Nov. 20, 2000, entitled "Systems and Methods for Generating and Modulating Illumination Conditions;"

U.S. patent application Ser. No. 09/675,419, filed Sep. 29, 2000, entitled "Systems and Methods for Calibrating Light Output by Light-Emitting Diodes;"

U.S. patent application Ser. No. 09/870,418, filed May 30, 2001, entitled "A Method and Apparatus for Authoring and Playing Back Lighting Sequences;"

U.S. patent application Ser. No. 10/045,629, filed Oct. 25, 2001, entitled "Methods and Apparatus for Controlling Illumination;"

U.S. patent application Ser. No. 10/158,579, filed May 30, 2002, entitled "Methods and Apparatus for Controlling Devices in a Networked Lighting System;"

U.S. patent application Ser. No. 10/325,635, filed Dec. 19, 2002, entitled "Controlled Lighting Methods and Apparatus;"

U.S. patent application Ser. No. 10/360,594, filed Feb. 6, 2003, entitled "Controlled Lighting Methods and Apparatus;" and U.S. Provisional Application Ser. No. 60/415,897, filed Oct. 3, 2002, entitled "Methods and Apparatus for Illuminating Environments."

DETAILED DESCRIPTION

Figure 1:
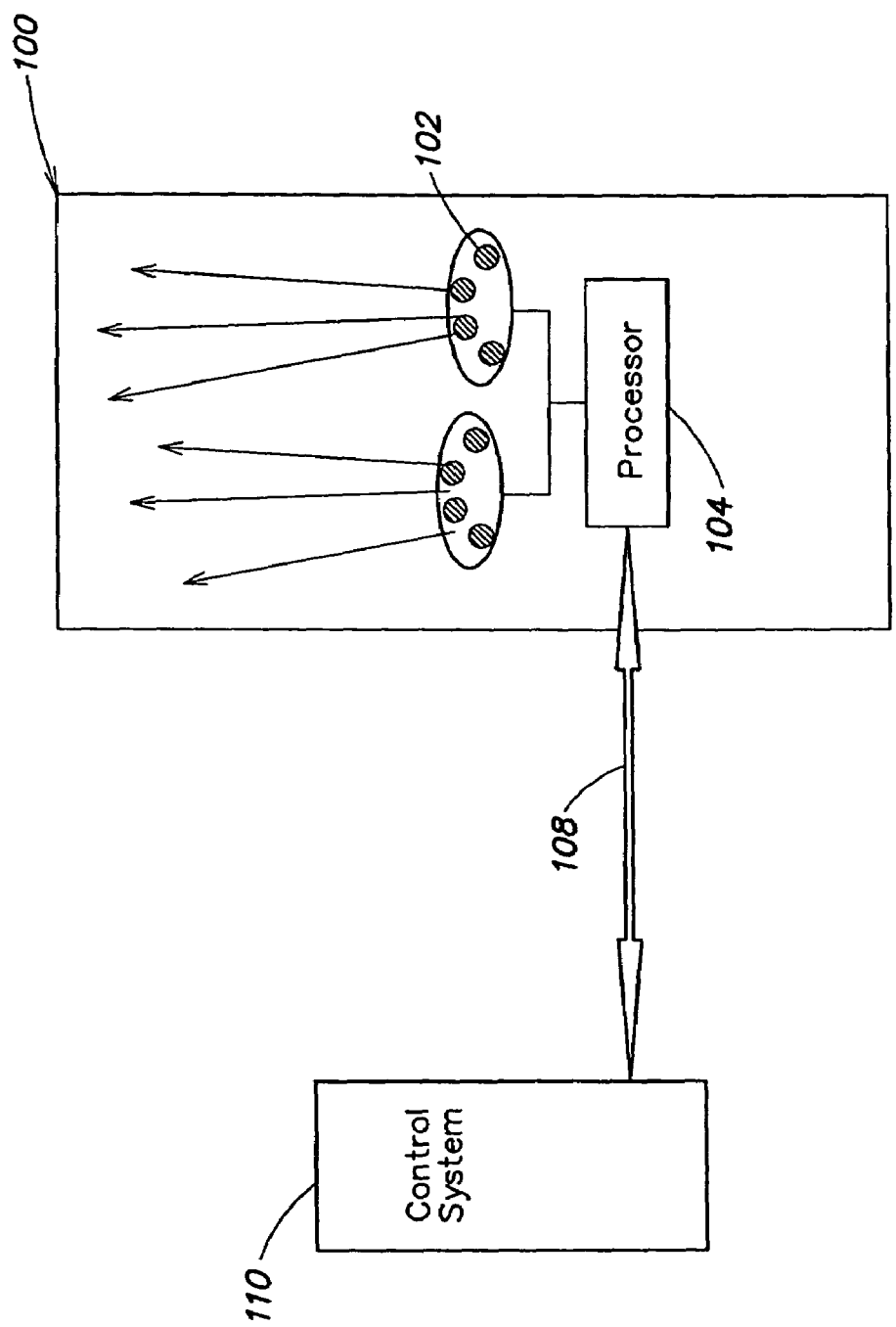
FIG. 1 depicts a group of LEDs under the control of a processor for providing color changing illumination.

FIG. 1 depicts an illumination system 100 with a group of lights 102 under the control of a processor 104 for providing color-changing illumination. Control can be provided through a wide variety of facilities. Optional system elements can include facilities for networking light systems 100, including a network 108 (which can be a wired or wireless network, bus, circuit, or similar facility) and a control system 110, which could be a personal computer or other computer system. Methods and systems for networked and non-networked computer control of illumination systems 100 are described in the patents and patent applications referenced above and incorporated by reference herein.

The lights 102 can be LEDs or other illumination systems. In preferred embodiments, LEDs can be used.

An illumination system 100 consisting of a plurality of LEDs 102 combined with a processor 104 can be disposed in many different environments, including those that relate to household products.

Figure 2:
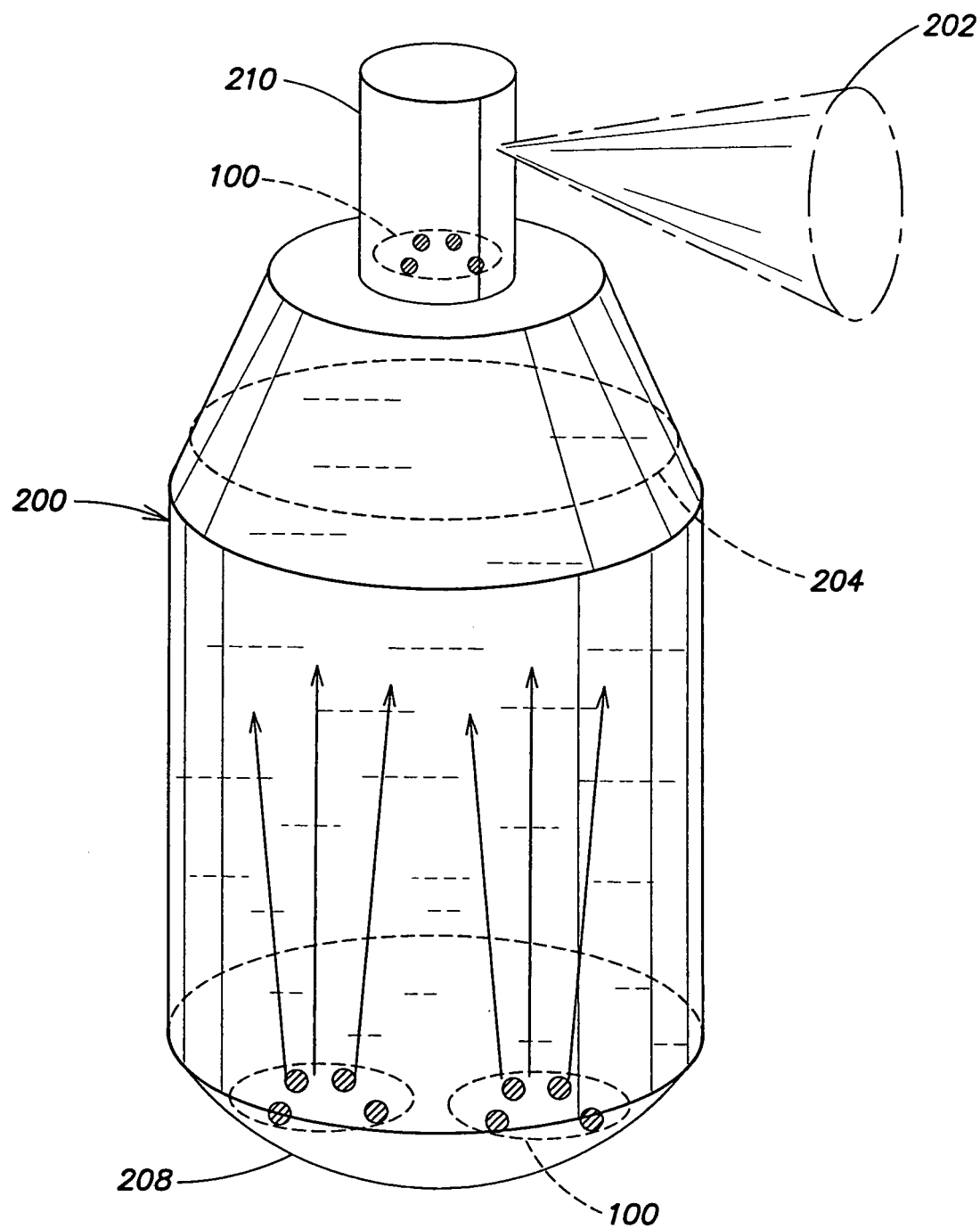
FIG. 2 depicts a spray container with optional light systems for providing an illumination facility.

FIG. 2 depicts a spray container 200 with light systems 100 for providing illumination to different portions of the spray container 200. The spray container 200 generates a spray 202 of a fluid 204 that is stored in the interior of the spray container 200. Light systems 100 can be disposed in the bottom 208 of the container 200, in the neck 210 of the container 200, or elsewhere in the interior or on the exterior of the container 200. In embodiments, the container 200 is a can, such as an aerosol can.

In embodiments, the container 200 can be made of a clear material, so that the interior fluid 204 is illuminated by the light systems 100. The fluid 204 can be clear, or substantially transparent or translucent, so that it takes on a color that is altered by the light from the light systems 100 in the bottom 208 of the container 200.

In embodiments, the light systems in the neck 210 of the container 200 light the fluid 204 as it sprays from the container 200, so that the spray is an illuminated spray, optionally a color-changing illuminated spray.

The fluid 204 can be any fluid, such as fluid useful in a household products, such as water, ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, surface cleaner, and liquid wax.

Figure 3:
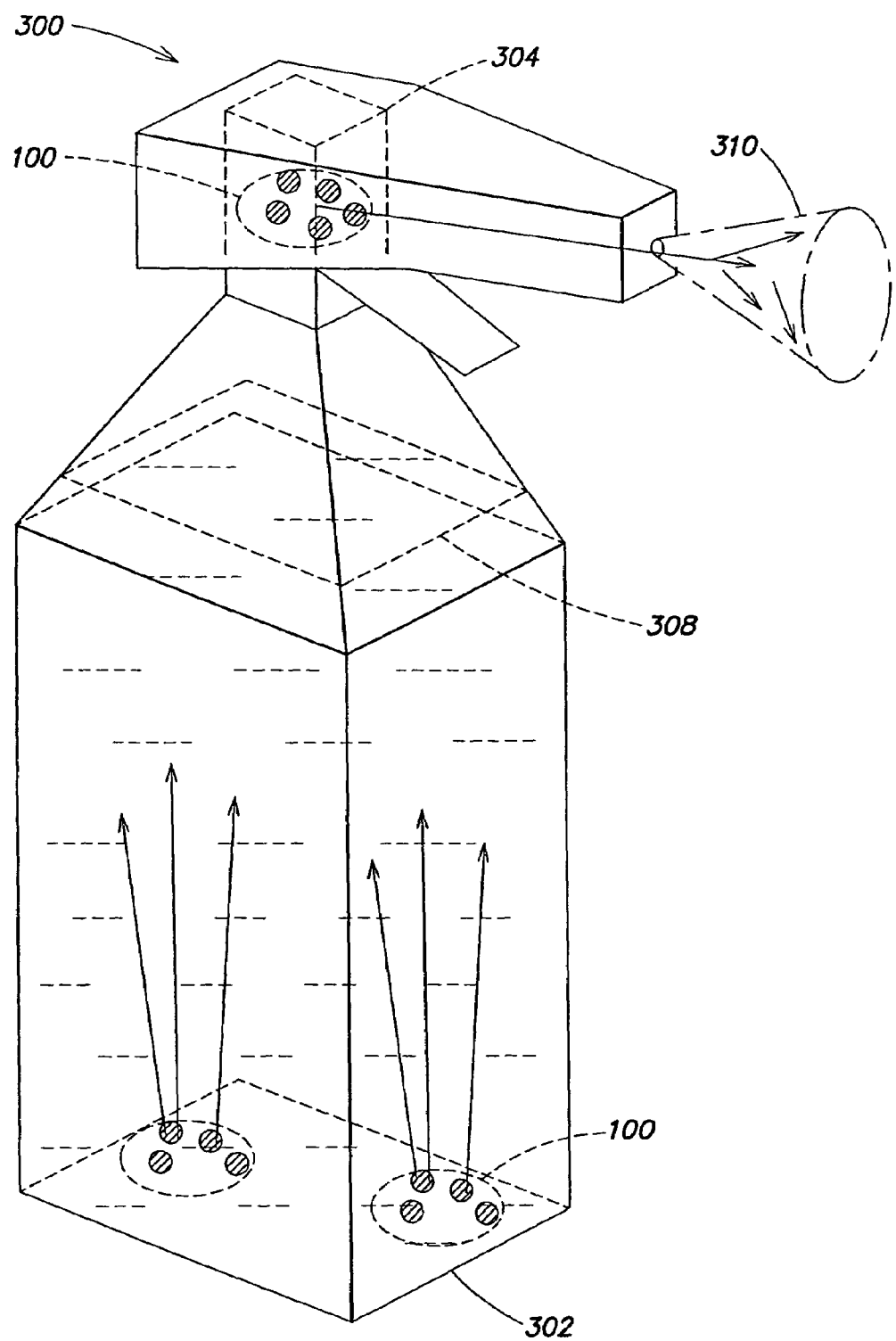
FIG. 3 depicts a spray bottle with light systems for providing an illumination facility.

FIG. 3 depicts a spray bottle 300 with light systems 100 for providing a illumination. The spray bottle 300 may include a bottom 302, with light systems 100 and/or a neck 304 with light systems 100. The light systems 100 in the bottom 302 can light a fluid 308 that is stored in the spray bottle 300. The bottle 300 can be clear, so that a light system 100 illuminates the fluid in colors. The light systems 100 in the neck 304 can illuminate a spray 310 of the fluid 308 in color-changing illumination conditions.

As with fluids in a can or similar container 200, the fluid 308 can be any fluid, such as fluid useful in a household products, such as water, ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, surface cleaner, after shave and liquid wax.

Thus, the fluid 308 can be illuminated either in the bottle 300 or in a spray 310 or stream that is sprayed from the bottle 300.

Figure 4:
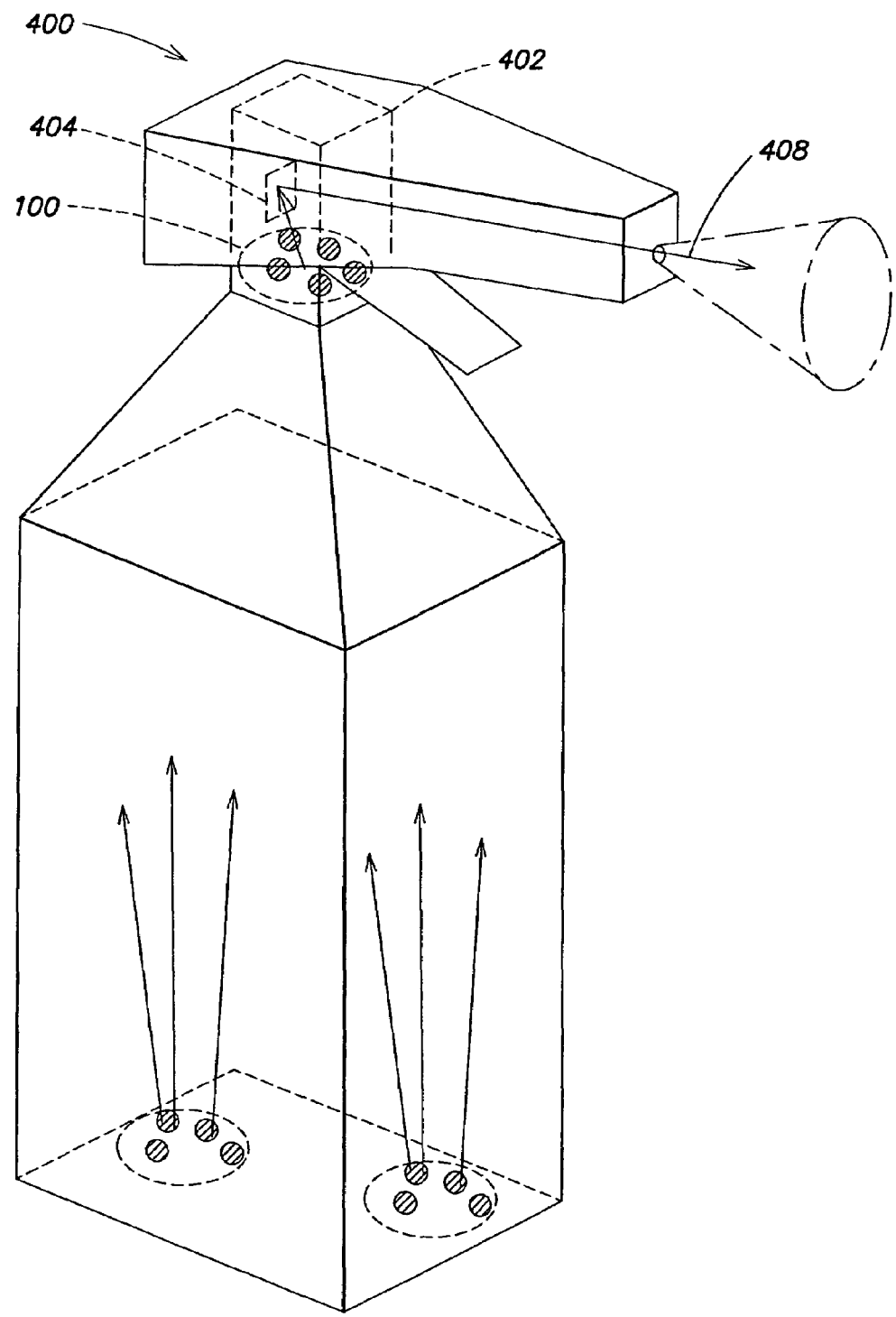
FIG. 4 depicts a spray bottle with a light system and an optics facility.

FIG. 4 depicts a spray bottle 400 with a light system 100 in the neck 402. The system also includes an optics facility 404, such as a mirror or lens, that reflects light from the spray bottle 400 in a ray 408. The ray 408 can illuminate a spray coming from the bottle, or it can be directed otherwise from the bottle 400, such as out the top, or down into the fluid in the bottle 400. The optics facility 404 is one of many optional optics facilities 404, such as mirrors, lenses, and the like, that can be used to manipulate light from a light system 100 disposed on or in a household product, such as a container 200, or bottle 300, 400.

Figure 5:
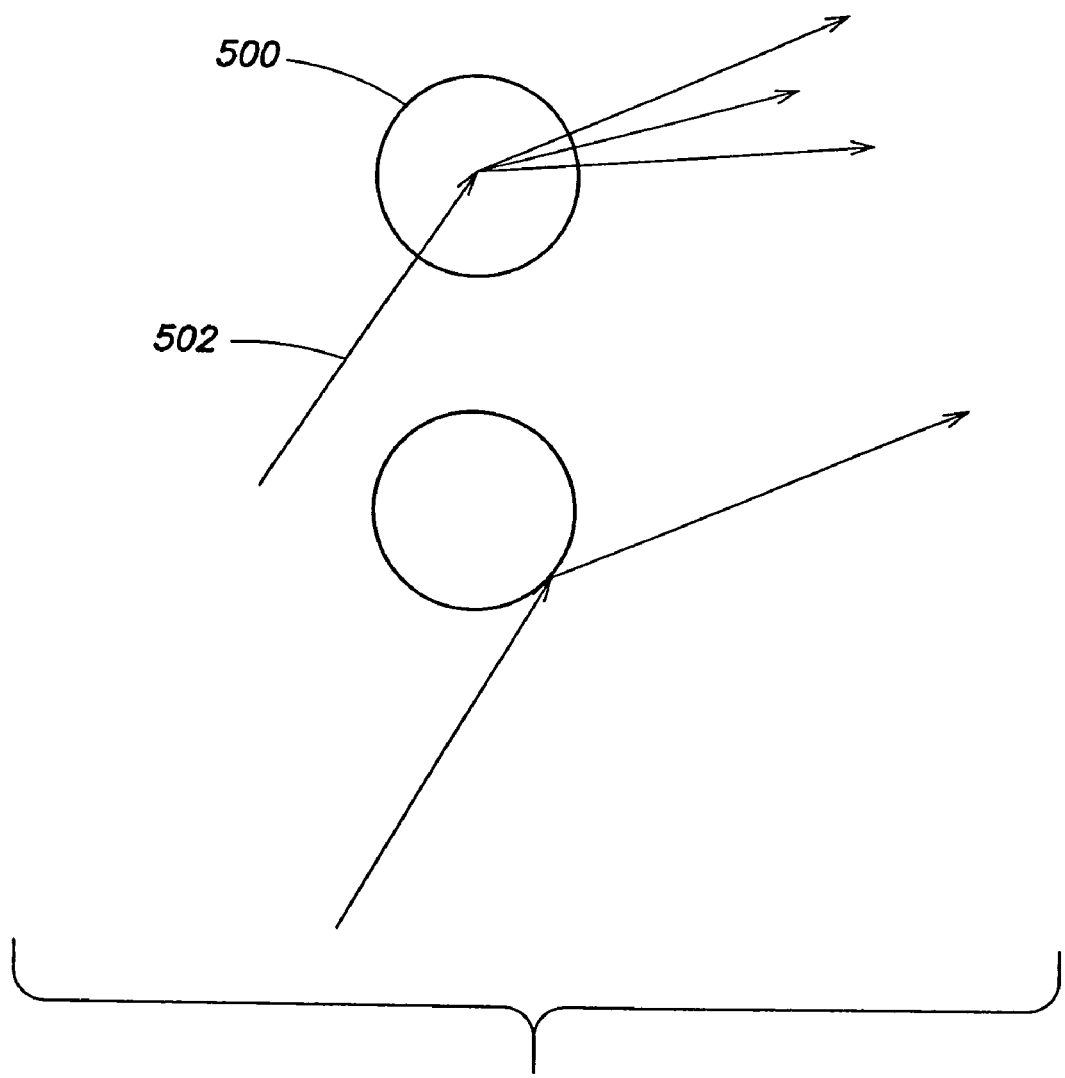
FIG. 5 depicts an optical effect of a liquid particle on a light ray.

FIG. 5 depicts an optical effect of a fluid particle 500 on a light ray 502. A fluid particle 500 can reflect or refract light 502, resulting in redirection of the light, and in some cases changing the color of the light, such as in a rainbow effect. Sprays and streams of fluid coming from a household products, faucet, or shower head can be illuminated by light systems 100, creating aesthetically pleasing effects, due to the interaction of light from the light systems 100 with the fluids.

Figure 6:
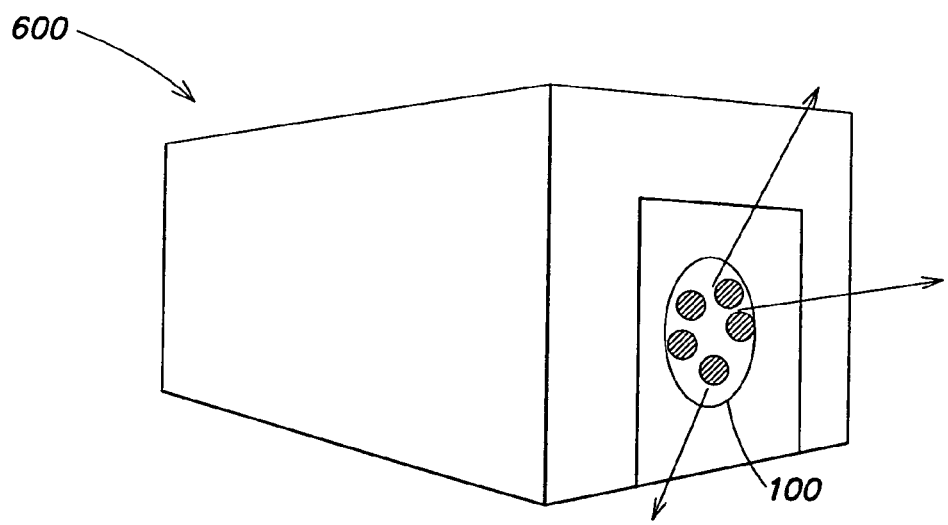
FIG. 6 depicts an insect control facility with an illumination facility.

FIG. 6 depicts an insect control facility 600 with an illumination facility. A light system 100 can be disposed on the insect control facility 600. Insects respond to light of different frequencies. The light from the light systems 100 can be used to attract or repel insects. The control facility 600 can be used in a roach motel, mosquito net, tiki torch, mosquito coil, bug zapper, deck light, pool light or other insect control facility 600.

Figure 7:
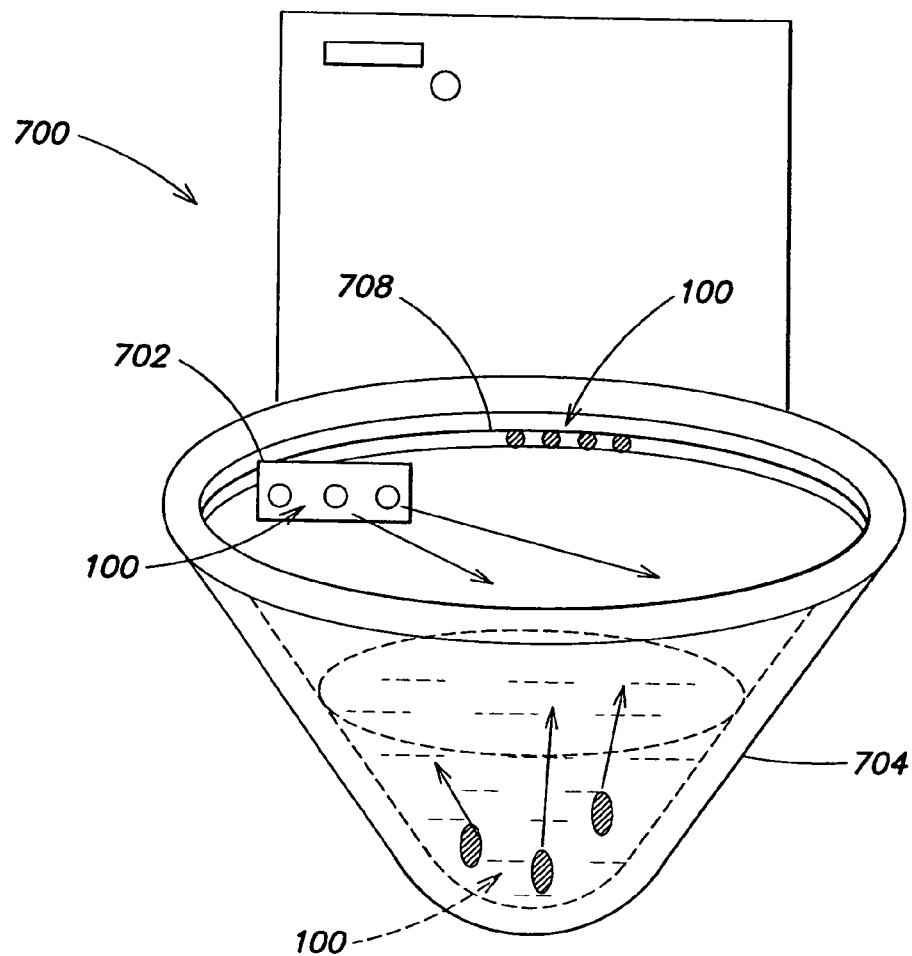
FIG. 7 depicts a toilet with an illumination facility.

FIG. 7 depicts a toilet 700 with an illumination facility. The toilet 700 can include one or more light systems 100. For example, a light system 100 can be disposed to light the water in the bowl 704. A light system 100 could also be used to light an odor control mechanism, such as a bar or puck 702 that is disposed in a rack above the bowl. A light system 100 can be disposed in a ring 708 in the bowl. A light system can be used to illuminate water in other locations in the house, such as a bathtub, sink or fountain.

In general, a light system 100 can be used to light any household object or appliance, such as a toilet, faucet, shower, tub, sink, appliance, refrigerator, oven, microwave, counter, drawer, cabinet, floor, ceiling, wall, chair, desk, table, washer, dryer, mixer, blender, toaster, or the like.

Figure 8:
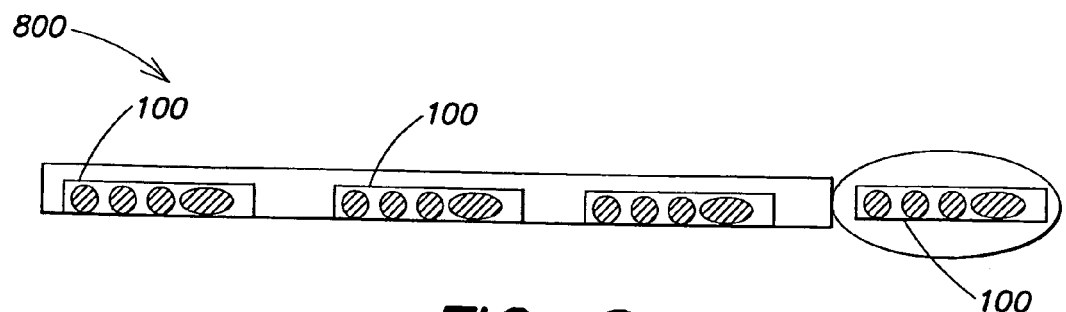
FIG. 8 depicts a toothbrush with an illumination facility.

Lights systems 100 can be used to provide color-controlled illumination to common household products. FIG. 8 depicts a toothbrush 800 with an illumination facility including light systems 100. The toothbrush can be provided with clear, transparent, translucent or similar materials to permit color changes through the light systems 100. Household products include a wide variety of items that can benefit from color changing effects, such as, in addition to the toothbrush, a pencil, a pen, a fork, a knife, a spoon, a kitchen utensil, a whisk, a broom, a bottle, a glass, a mug, a coffee maker, a toothpaste tube, a dispenser, a shampoo bottle, a soap holder, a razor, an electric razor, a hair dryer, a picture frame, a marker, a jar, a makeup facility, a perfume dispenser, a brush, a lipstick, and a candle.

Figure 9:
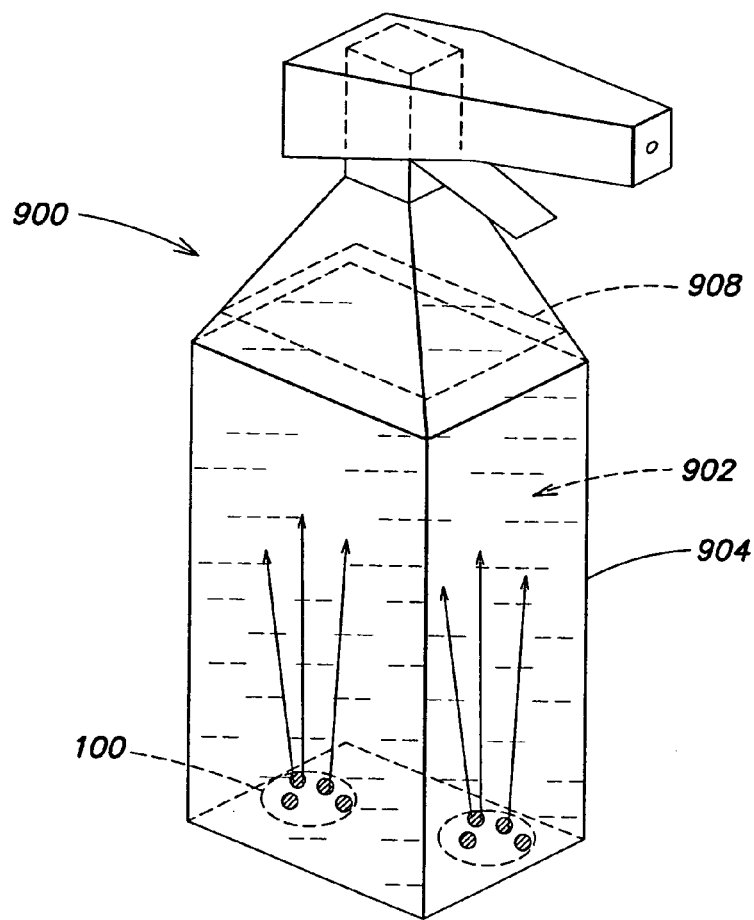
FIG. 9 depicts a liquid bottle with an illumination facility.

FIG. 9 depicts a bottle 900 with an illumination facility. The light systems 100 can light the interior 902 or exterior 904 of the bottle 900. The bottle 900 can be made of materials needed to allow the light systems 100 to provide attractive, aesthetic, or attention-getting effects. The light systems 100 can illuminate a fluid 908 in the interior. Lighting the fluid 908 can provide a pleasing effect, or can attract attention to the bottle on a merchandise shelf. The fluid in the bottle 900 can be any fluid, such as those described above, such as liquid soap, or another fluid, such as water, ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, after shave, surface cleaner, and liquid wax.

One use of a light system 100 in connection with a container 200, or bottom 300, 400 or 900, or in connection with any other disposable product or product with limited useful life, is as an indicator of a condition of the product. The light system 100 can be coupled with a sensor for sensing a condition of the product, or with a timer for measuring time, or the like. For example a light system can illuminate when a chemical product is no longer working well, such as an odor control chemical. A light system 100 can illuminate in a certain way when a product has reached a certain age. A light system 100 can illuminate in a certain way when a container is nearly empty. Thus, a light system 100 can be used to provide information to a consumer using a product, such as a household product, about the condition of the product itself. A wide range of product characteristics can be measured and indicated by light systems 100 under the control of a processor 104.

Figure 10:
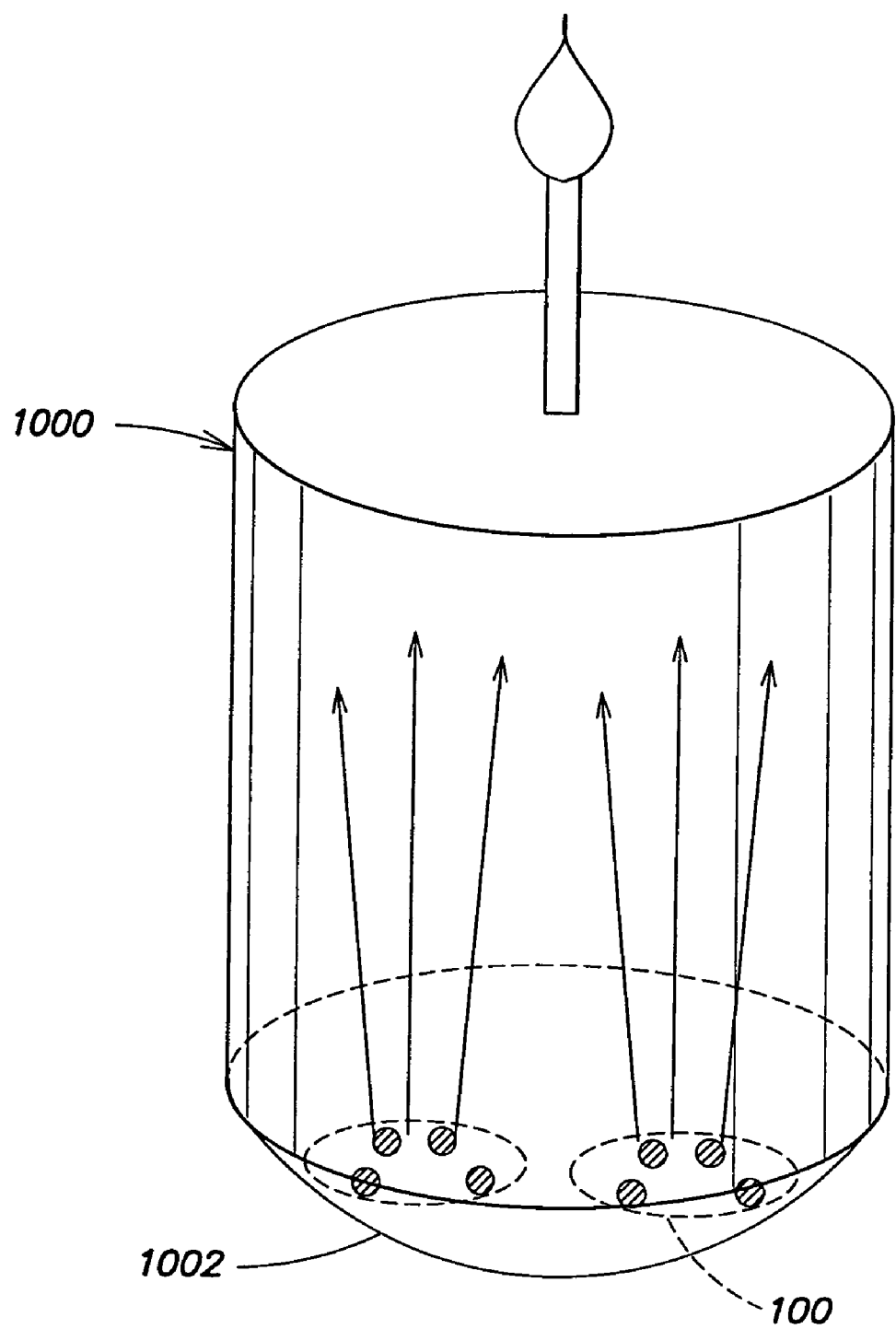
FIG. 10 depicts a candle with an illumination facility in a removable base.

FIG. 10 depicts a candle 1000 with an illumination facility in a removable base 1002. The light systems 100 illuminate the candle 1000, providing color-changing effects. The base 1002 can hold the light systems 100, so that disposable candles 1000 can be used with one base 1002. Many other disposable household objects can be disposed on a base 1002 to provide illumination, such as odor control items, scent-producing items, sprays, fluids, soaps and the like. A glass can be disposed on the base 1002 to illuminate any fluid in it, such as those described above.

Figure 11:
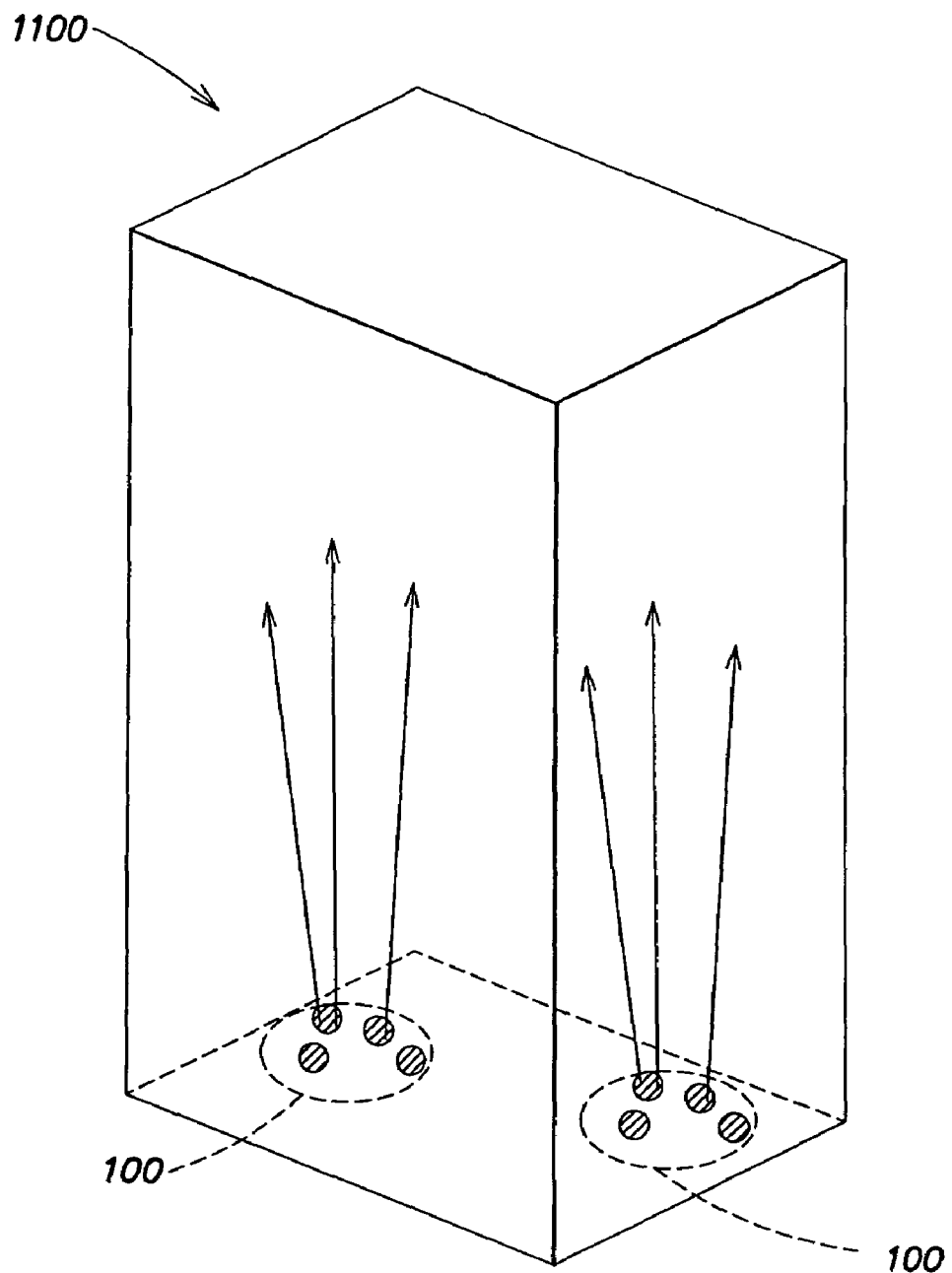
FIG. 11 depicts a package for merchandise with an illumination facility.

FIG. 11 depicts a package 1100 for merchandise. The package 1100 can include light systems 100 to provide an illumination facility for the package 1100. The package 1100 can be illuminated on the shelf to attract attention to any product or merchandise, such as any product that can be provided in a can, container, or box. The product can be a household cleaner, wax, shampoo, soap, razor, toothbrush, skin care product, or any other household or other product described herein or found on retail shelves.

Figure 12:
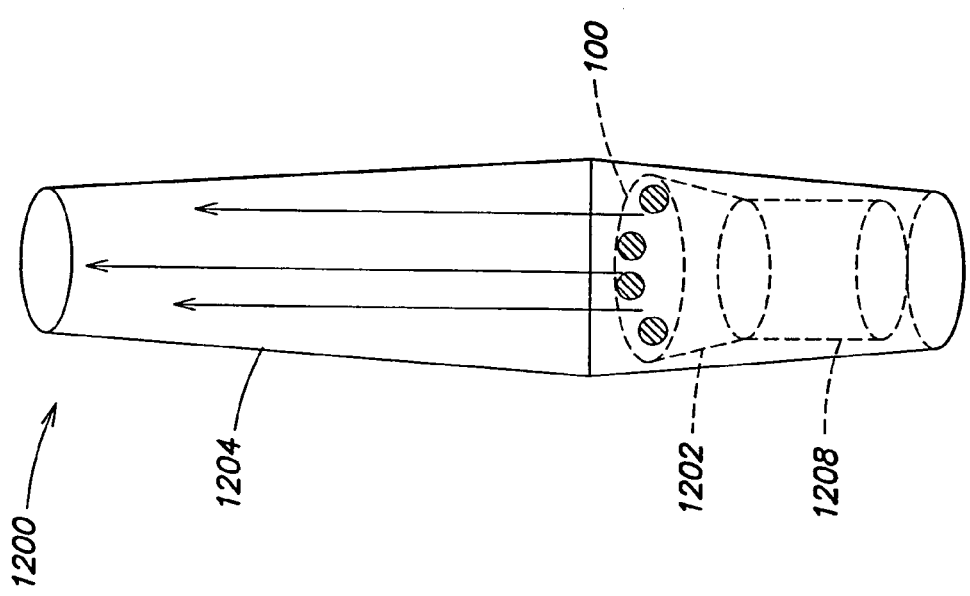
FIG. 12 depicts a wand with an illumination facility and a spray facility.

FIG. 12 depicts a wand 1200 with a light system 100 for illumination and a spray facility 1202. The wand 1200 includes a housing 1204 that is translucent or transparent, so that it glows in the color produced by light from the light system 100. The wand 1200 also includes a spray facility 1202 for spraying a fluid from a reservoir 1208. The fluid can be any fluid, such as those mentioned above. In an embodiment, the wand sprays insect repellant, and the light system 100 illuminates the spray, as well as the exterior housing 1204 of the wand 1200.

Figure 13:
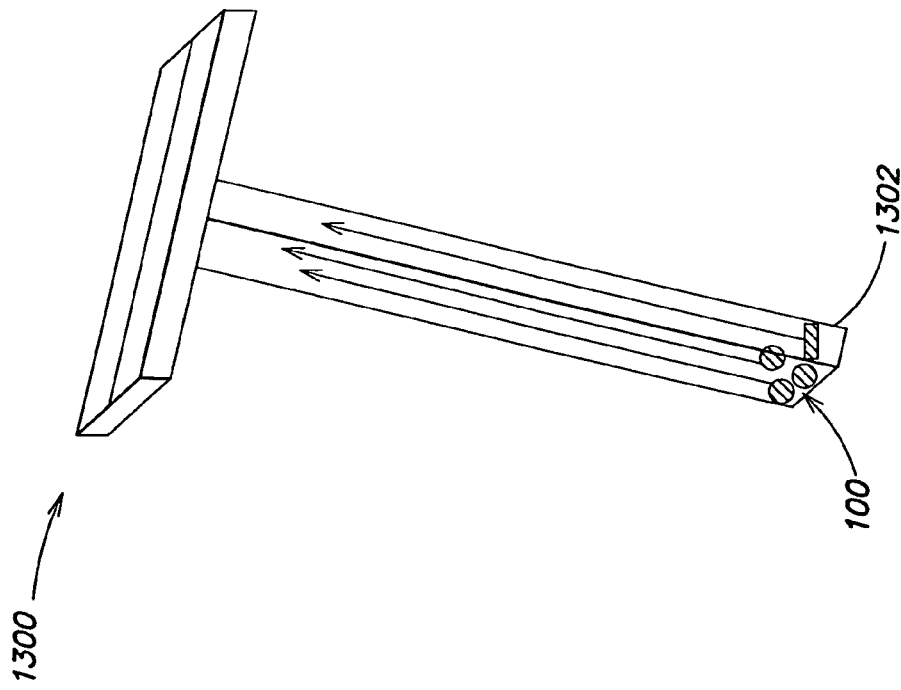
FIG. 13 depicts a razor with an illumination facility.

FIG. 13 depicts a razor 1300 with an illumination facility. A light system 100 lights a housing 1302, which may be made of transparent or translucent material, so that the light system 100 changes the color of the housing 1302 under control of a processor 104 (not shown) of the light system 100.

Figure 14:
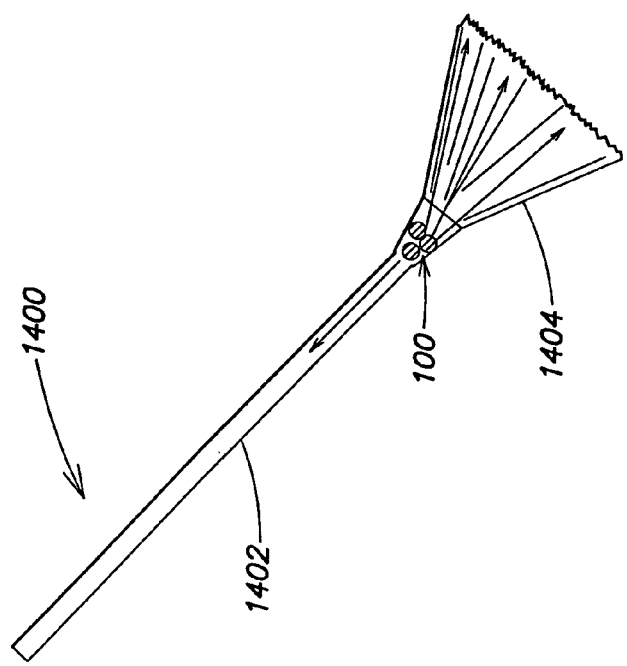
FIG. 14 depicts broom with an illumination facility.

FIG. 14 depicts broom 1400 with an illumination facility. A light system 100 is disposed in the handle 1402 of the broom 1400. The light system 100 can light the handle 1402, which can be made of a transparent or translucent material to accept color changes from the light system 100. The light system 100 can also be used to light in another direction, such as toward the floor when the broom 1400 is in use. The broom 1400 could be a push broom, hand broom, brush, or similar facility with a handle 1402 and bristles 1404.

Figure 15:
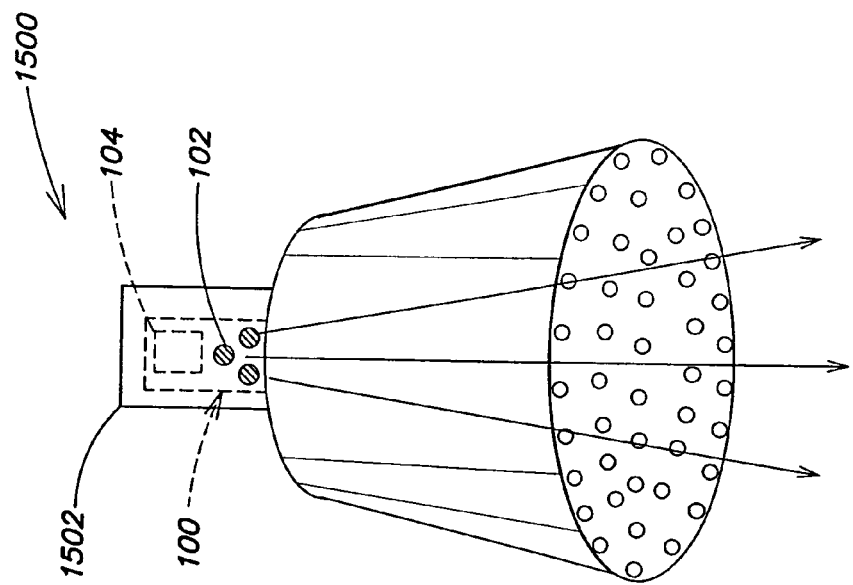
FIG. 15 depicts a showerhead with an illumination facility.

FIG. 15 depicts a showerhead 1500 with an illumination facility. A light system 100 with lights 102, such as LEDs, and a processor 104, can be disposed in the neck 1502 of the showerhead. The light system 100 can illuminate the water spray from the showerhead 1500. Similarly, a light system 100 could be used to illuminate a water spray from a faucet, such as that of a sink or tub.

Figure 16:
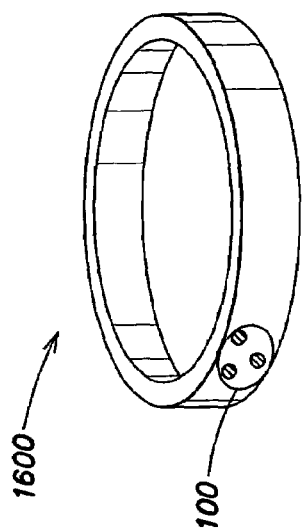
FIG. 16 depicts an animal collar with an illumination facility.

FIG. 16 depicts an animal collar 1600 with an illumination facility. A light system 100 can illuminate the collar, or illuminate the area around the collar. The collar can be a flea collar or similar insect control collar, or it can be a conventional collar.

Figure 17:
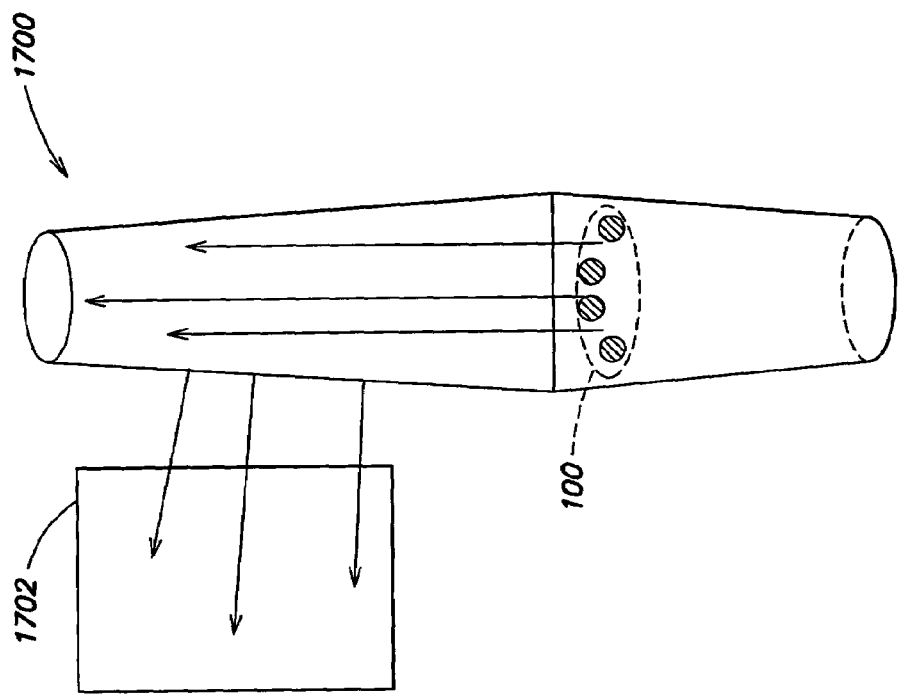
FIG. 17 depicts an illumination facility for use in interaction with an application of a chemical.

FIG. 17 depicts an illumination facility 1700 for use in interaction with an application of a chemical 1702. Light from the illumination facility 1700 can be provided in any color of the spectrum, under control of a processor 104. Thus, the light can interact with the chemical 1702 to create an effect. For example, a chemical can include a luminescent portion that lights under light of a given spectrum. Such a luminescent facility could be used to confirm, with an illumination facility 1700 that a chemical has been applied over all of a given surface, such as a surface covered with insect repellant, a deck sealer, or a suntan lotion.

Figure 18:
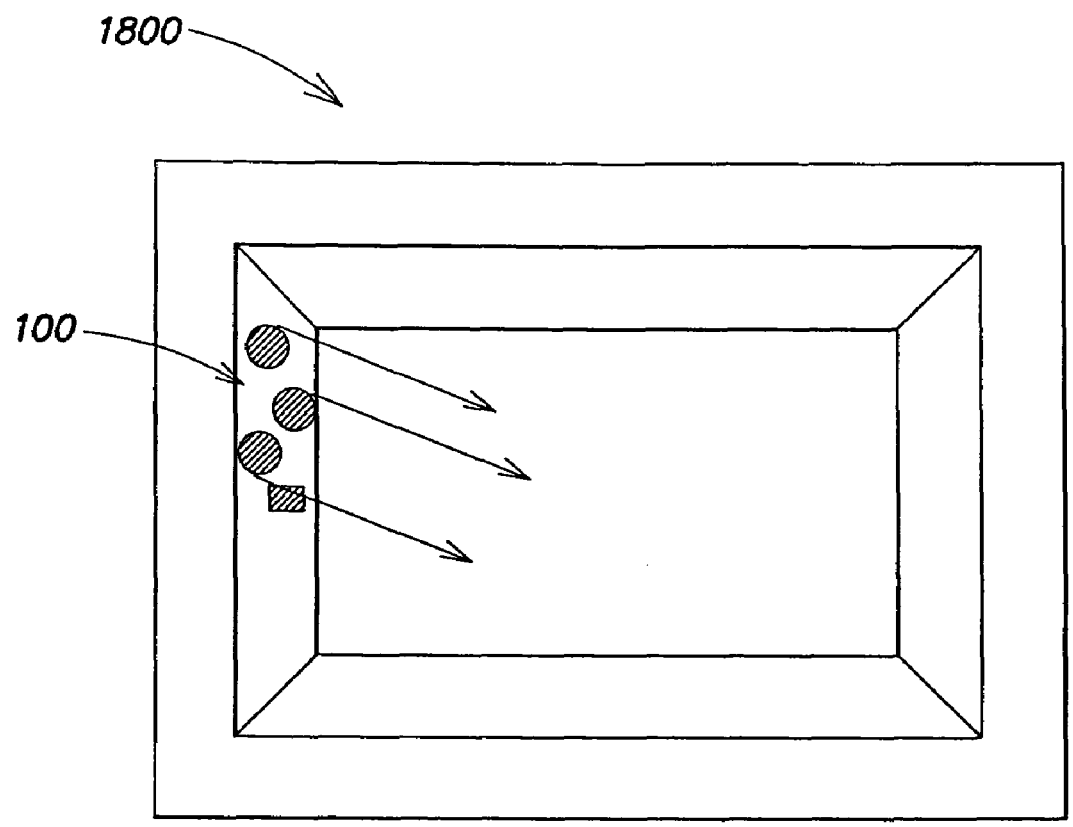
FIG. 18 depicts an appliance with an illumination facility.

FIG. 18 depicts an appliance 1800 with an illumination facility. The appliance 1800 may be an oven, microwave oven, refrigerator, washer, dryer, toaster, or other appliance. The light system 100 can be used to light the appliance 1800 or an interior or exterior environment of or about the appliance 1800. The light system 100 can be coupled with a sensor to sense an environmental condition and to display illumination that indicates the condition. For example, an oven can light in a red color if it is hot. Sensor and feedback applications are described more particularly in certain patents and patent applications incorporated by reference herein.

In yet another embodiment of the present invention, an illumination system is disposed in combination with a scent-producing facility. Together with a processor or processors, this combination allows simultaneous or coordinated production of controlled scent and illumination. In embodiments, the scent/illumination device can be employed in conjunction with a network. In embodiments, the device may be provided with addressable control facilities. In embodiments, the devices can be employed using data delivery protocols such as DMX and power protocols such as pulse width modulation. In embodiments, the devices may be equipped with a communications facility, such as a transmitter, receiver, transceiver, wireless communications facility, wire, cable, or connector. Thus, the device can store, manipulate and otherwise handle data, including instructions that facilitate controlled illumination or controlled scent, or both. The device may also, in embodiments, receive control signals from another source, such as a user interface, an external computer, a sensor, or the like.

A wide variety of illumination and display effects can be employed in connection with the scent producing facility, ranging from color washes, to rainbow effects, to rapid changes in color, and the like. The scents can also be controlled whereby different chemicals are triggered to respond to an input signal (e.g. Digiscents Inc. multi-scent devices) and a 'smell wash' or smell sequence synchronous with a color wash or color sequence can be activated.

In other embodiments, the illumination can reflect a sensed condition, such as a condition sensed in the environment of the scent-producing facility. In other embodiments, the illumination can reflect a condition of the scent-producing facility, such as remaining life of the device, the remaining amount of scent-producing materials or chemicals, the quality of the scent, the strength of scent, battery life, or the like.

The scent-producing facility may be an air freshener or other scent-producing facility that may optionally plug into a room outlet. In embodiments, the scent may be varied in response to data received by the device, as controlled by a processor that also controls the illumination.

The scent-producing facility can be programmed to produce scents in concert with the illumination; thus, a scent may be correlated with illumination that reflects a similar aesthetic condition, emotional state, environmental condition, data item, or other object or characteristic. For example, a pine scent could be coupled with green illumination, while a pumpkin scent could be coupled with orange illumination. Thus, a wide range of correlated colors and scents can be provided in a device where one or more processors controls both scent and illumination.

In an embodiment, the device is a combined air freshener and color-changing night-light, with a processor for control of the illumination condition of the night light, and with LEDs providing the source of illumination for the night light.

In an embodiment, a gel may be presented and a color changing illumination system may be directed to illuminate the gel. For example, there are many fragrances, deodorants, and the like that are made into gels. This gel can be made into most any shape and an illumination system may be used to project light through the gel. In an embodiment, the gel may appear to be glowing in colors.

In an embodiment, the gel or other material may evapaorate over time and as the material evaporates, the light levels captured by the material may diminish. This will result in the light levels decreasing as the material evaporates giving an indication of material life. In an embodiment, the light may actually appear when the evaporation, or other process, has removed a portion of the material.

In an embodiment, the illumination may be associated with a sensor. Such a sensor may measure or indicate germ, bacteria or other contamination levels and cause an illumination system to emit certain lighting conditions. An embodiment may be a color changing "germ alert sensors" that would hang in the toilet or trashcan, etc. Example: as your tidy bowl reached the terrifying point of not flooding the sewer lines with chlorine at every flush, your tiny tricolor LED would pulse RED hues to alert you.

Another aspect of the present invention is providing light from an apparatus that is coordinated with a scent generation portion of the apparatus. For example, the apparatus may be a plug-in style air freshener and the light produced by the air freshener may be colored to coordinate with the type of scent being emitted. The light emitted from an evergreen scented air freshener may be greenish blue for example. Another aspect of the present invention is providing an indication of useful life of a portion of a system. The system, an air freshening system for example, may have a life limited air cartridge and an indication of life may be provided. The indication of life may be provided through a certain lighting pattern for example.

Figure 19:
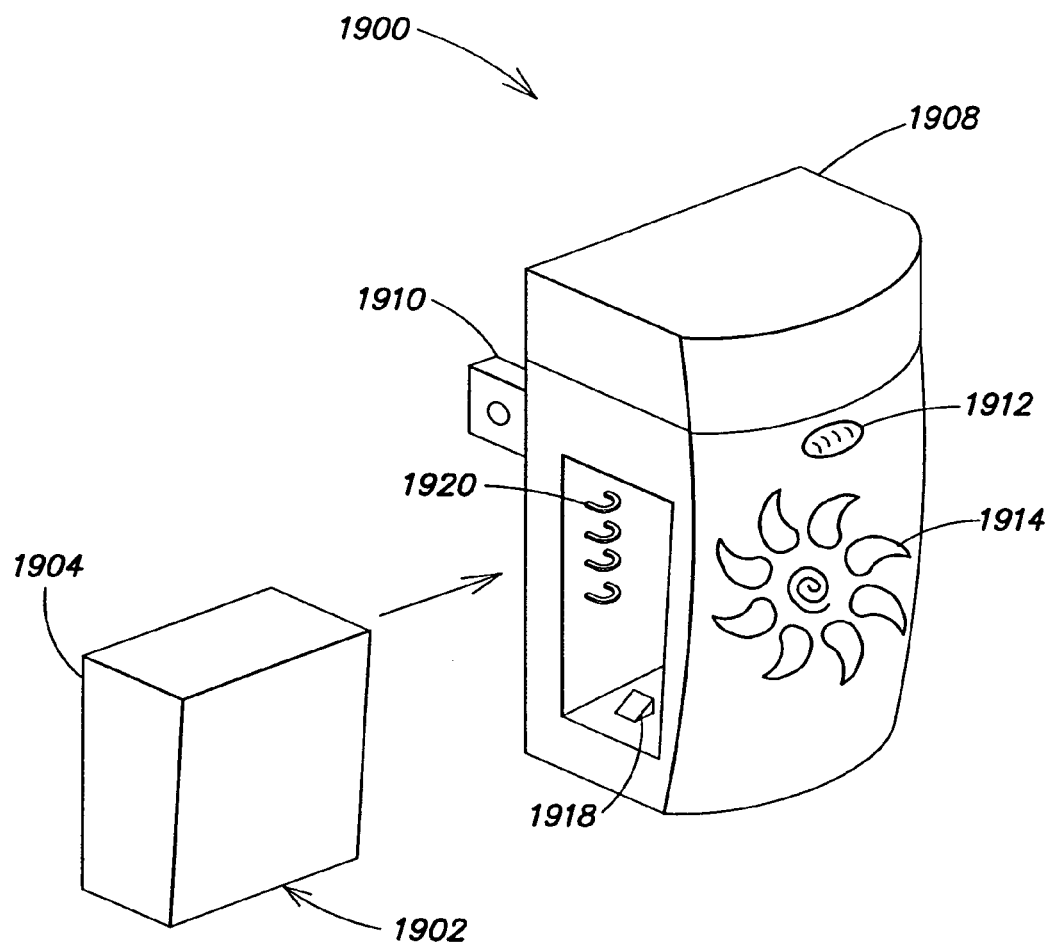
FIG. 19 illustrates one example of a scent producing apparatus incorporating an illumination source, according to one embodiment of the invention.

An embodiment of the present invention is a scent producing apparatus 1900 with an illumination source 100. One such device is illustrated in FIG. 19. The illumination source, or system, may be similar to that described above as illumination system 100. The illumination system 100 may be arranged to produce color controllable illumination through an optic 1908 for example. The scent producing apparatus 1900 may be adapted to plug into a conventional wall power outlet through an adapter 1910. The apparatus 1900 may include a vented portion 1914 to facilitate the emission of scent from a scent cartridge 1902 once installed.

According to one aspect of the invention, the scent producing apparatus 1900 may be adapted to read, or otherwise identify, certain characteristics of the scent cartridge. For example, it may identify the type of cartridge, the scent to be produced by the cartridge, the date of manufacture, date of installation, serial number or other parameter. In an embodiment, the scent producing apparatus may be adapted to alter the color, pattern, intensity or other parameter of the light emitted by the illumination system 100. For example, the cartridge 1902 may be encoded to identify the type of scent it produces. The scent producing apparatus 1900 may read the code and alter the light it produces to match the type of scent. The scent may be deemed an evergreen scent and the light emitted from the illumination system 100 may be altered to be green or blue for example. The light may also have a temporal effect such as to alternate between a green and blue or generate some other pattern intended to coordinate with the scent.

In another embodiment, the scent producing apparatus 1900 may also monitor the duration the cartridge 1902 is in the scent producing apparatus 1900 or otherwise monitor the effectiveness of the cartridge. Once the effectiveness, or lapsed time, indicates the cartridge should be changed, the illumination system 100 may be adapted to change the lighting pattern, color, intensity or other parameter it is producing. This method of operation may be useful indicating to a user that the cartridge is due to be changed. In an embodiment, the apparatus 1900 may include a user interface 1912, much like the user interface identified above. The user interface 1912 may be used to override the indication light to provide normal illumination or alter the illumination to accommodate his/her desires. In an embodiment, the illumination system 100 may be adapted to stay in an override operation mode for a preset period of time. For example, the preset period may be three days, such that the light stays in the override lighting pattern for three days and then automatically converts back to the end of usefulness indication. This may be useful to allow a user to go into an override mode for a period of time but automatically be reminded that the cartridge needs to be renewed. In an embodiment, the user may set the time of the override and/or the user may have the option of electing an override period that does not automatically end.

Figure 20A:
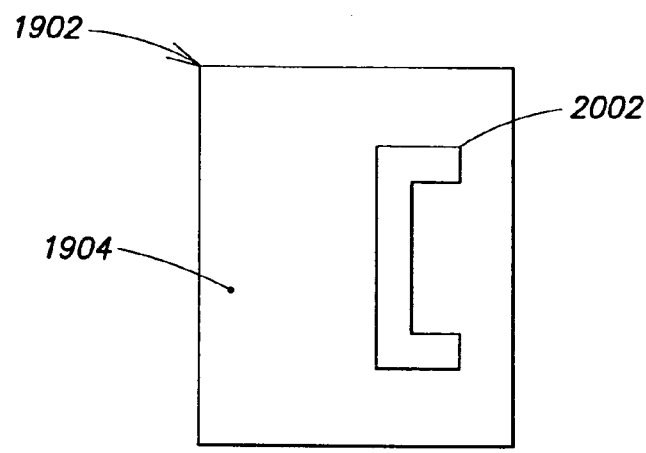
FIGS. 20A, B, and C illustrate various features related to a scent cartridge of the apparatus of FIG. 19, according to one embodiment of the invention.

In an embodiment, the apparatus 1900 may have a set of contacts 1920. The contacts 1920 may be associated with a processor in the apparatus 1900 (e.g. processor 104 of the illumination system 100). The processor 104 may be adapted to monitor the contacts 1920 for activity or association characteristics with a cartridge 1902. For example, the contacts 1920 may be on a rear interior wall of the apparatus 1900 and the cartridge 1902 may have conductive strips 2002 on the rear wall 1904 of the cartridge 1902. The illustrations in FIG. 20 A and B show different patterns of conductive strips 2002 on the rear wall 1904 of the cartridge 1902. The illustration in FIG. 20 A may represent the conductive strip pattern associated with an evergreen scent cartridge while the illustration in FIG. 20 B may represent a raspberry scent cartridge. When a cartridge 1902 with the pattern 2002 of FIG. 20A is inserted into the apparatus 1900, the contacts 1920 will sense the pattern and the processor 104 can adjust the color of the light emitted accordingly. For example, the bottom protrusion of pattern 2002 may be aligned with one of the contacts 1920 in an array of contacts and the upper protrusion of pattern 2002 may be associated with another contact 1920 of the array. Depending on the placement of the upper pattern, for example, may dictate which contact in the array is associated with the pattern. The processor 104 may then recognize the pattern and adjust the lighting accordingly. This is but one example of a system designed to recognize a cartridge type of many that are envisioned by the applicant and encompassed by the present invention. For example, FIG. 20 C illustrates another such method.

Figure 20B:
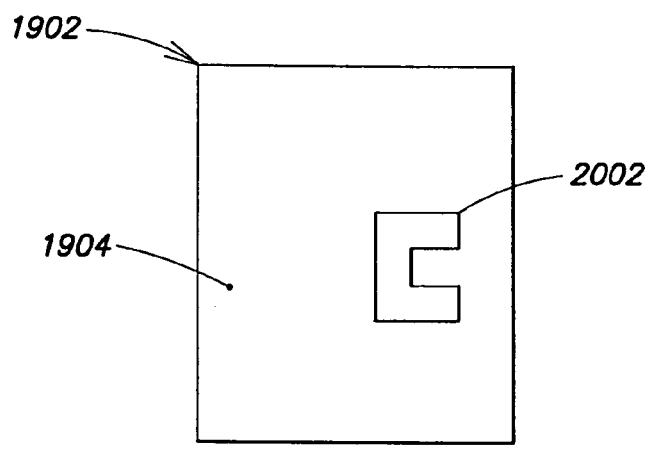
Figure 20C:
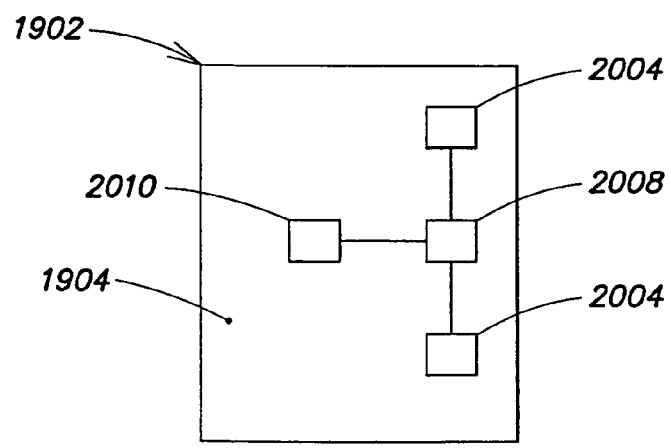

FIG. 20 C illustrates the rear wall 1904 of a cartridge 1902. The rear wall 1904 may include three electrically conductive pads. Pads 2004 may be designed to bring power to a circuit on the cartridge 1902 and the third pad 2010 may be a data pad for the circuit. These three pads may be associated with a circuit (e.g. integrated circuit 2008) and the integrated circuit may be adapted to output data to the data pad, which in turn may be associated with the processor 104 in the apparatus 1900. The integrated circuit may be adapted to produce data indicative of the cartridge type, scent, manufacturing date, installation date, lapsed time that the cartridge received power (e.g. measure of time in use), or other parameter. The circuit may include a counter and once the counter reaches a particular point it may indicate it is time to change the cartridge through a display of a certain lighting pattern, or it may make a sound or provide some other type of alert. The timing system may provide several indications of remaining usefulness so the user can become informed as to the state (e.g. the cartridge is 80% spent) and time the replacement accordingly.

In an embodiment, the apparatus 1900 may be programmed to display a color of light that is an indication of useful remaining life of the cartridge. For example, the light may be blue when the cartridge is new or full and it may gradually, or in some other predetermined way, change through a rainbow of colors until it reaches red where red indicates the cartridge has reached the end of its useful life. The user interface 1912 may allow a user to select such a mode, for example.

In an embodiment, the apparatus 1900 may include a switch 1918 where the switch 1918 is depressed, or otherwise activated, when the cartridge 1902 is loaded into the apparatus. The processor 104 may monitor the activation of the switch 1918 as an indication of the cartridge 1902 being loaded. From this indication, the apparatus 1900 may monitor or predict certain events. For example, the processor 104 may begin a timing circuit in an effort to predict the useful life of the cartridge 1902. In an embodiment, the switch may be associated with a mechanism or circuit to indicate whether the cartridge has been removed during a power down cycle. For example, the switch may be associated with a dial where the position of the dial can be read. When the apparatus 1900 is re-powered, the processor 104 may check the dial position and compare to the position indication of the dial before power-down to indicate if the cartridge has been removed. If the cartridge was removed, the processor may automatically start a new timer for the prediction of cartridge life expectancy. In an embodiment, the processor may also provide an indication (e.g. certain lighting pattern) that it believes the cartridge has been changed and ask for a user confirmation through the user interface 1912.

While the invention has been described in connection with certain preferred embodiments, other embodiments will be readily understood by those of ordinary skill in the art and are encompassed herein.

The invention claimed is:

1. A method of providing illumination for a household fluid product not intended for human consumption and/or a container that contains the household fluid product, the method comprising:
   providing at least one light system, comprising at least one light source controllable by a processor for generating a variable color radiation;
   disposing the at least one light system in proximity to the container so as to illuminate the container and/or the household fluid product with the variable color radiation, when generated; and
   generating a selected color of the variable color radiation in response to a signal from the processor so as to cause a color change of the container and/or the household fluid product.

2. The method of claim 1, wherein the step of disposing the at least one light system in proximity to the container includes disposing the at least one light system in at least one of the bottom of the container, the neck of the container, the interior of the container, the top of the container, and the nozzle of the container.

3. The method of claim 1, wherein the household fluid product is selected from the group consisting of ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, surface cleaner, and liquid wax.

4. The method of claim 1, wherein the signal relates to data indicative of a condition of the household fluid product.

5. The method of claim 4, wherein the data relates to the freshness of the household fluid product.

6. The method of claim 4, wherein the data relates to the efficacy of the household fluid product.

7. The method of claim 1, wherein the processor is responsive to a network.

8. The method of claim 1, wherein the processor responds to data directed to an address.

9. The method of claim 1, wherein the processor is responsive to a sensor.

10. The method of claim 1, wherein the selected color has a color temperature of white illumination.

11. The method of claim 1, wherein the container comprises an optical facility for operating on light generated by the light system.

12. The method of claim 11, wherein the optical facility is selected from the group consisting of a lens, a mirror, a liquid lens, a spinning mirror, a fresnel lens, a convex lens, a concave lens, a fiber optic, and a light pipe.

13. A method of providing illumination for a fluid, the method comprising:
providing a light system, comprising at least one light source controllable by a processor for generating a variable color radiation;
disposing the light system in proximity to a nozzle of a spray container containing the fluid;
discharging a portion of the fluid though the nozzle of the spray container; and
illuminating the portion of the fluid with a selected color of the variable color radiation.

14. The method of claim 13, further comprising producing a rainbow effect on the portion of the fluid.

15. The method of claim 13, further comprising changing the color of the portion of the fluid in response to the processor.

16. The method of claim 13, wherein the spray container is an aerosol can.

17. A system for providing illumination for a household fluid product not intended for human consumption and/or a container that contains the household fluid product, the system comprising:
at least one light system, comprising at least one light source controllable by a processor for generating a variable color radiation, the light system disposed proximate to the container and configured to generate a selected color of the variable color radiation in response to a signal from the processor to illuminate the container and/or the household fluid product with the selected color of the variable color radiation.

18. The system of claim 17, wherein the at least one light system is disposed in at least one of the bottom of the container, the neck of the container, the interior of the container, the top of the container, and the nozzle of the container.

19. The system of claim 17, wherein the household fluid product is selected from the group consisting of ammonia, bleach, window cleaner, insect repellant, insect killer, lotion, soap, liquid soap, kitchen cleaner, bathroom cleaner, shaving gel, cleaning fluid, lighter fluid, furniture polish, wood treatment, paint, primer, drain cleaner, disinfectant, room deodorizer, carpet deodorizer, room scent, perfume, cologne, shaving foam, toilet cleaner, aerosol, skin care fluid, suntan lotion, shampoo, surface cleaner, and liquid wax.

20. The system of claim 17, wherein the signal relates to data indicative of a condition of the household fluid product.

21. The system of claim 20, wherein the data relates to the freshness of the household fluid product.

22. The system of claim 21, wherein the data relates to the efficacy of the household fluid product.

23. The system of claim 17, wherein the processor is responsive to a network.

24. The system of claim 17, wherein the processor responds to data directed to an address.

25. The system of claim 17, wherein the processor is responsive to a sensor.

26. The system of claim 17, wherein the selected color has a color temperature of white illumination.

27. The system of claim 17, wherein the container further comprises an optical facility for operating on light generated by the light system.

28. The system of claim 27, wherein the optical facility is selected from the group consisting of a lens, a mirror, a liquid lens, a spinning mirror, a fresnel lens, a convex lens, a concave lens, a fiber optic, and a light pipe.

29. The system of claim 17 wherein the at least one light source comprises a plurality of LEDs of different colors, of which at least one first color LED radiates at a first wavelength different from a second wavelength at which at least one second color LED radiates.

30. A system for providing illumination for a fluid, comprising:
at least one light system, comprising at least one light source controllable by a processor for generating a variable color radiation, the system disposed proximate to a nozzle of a spray container, containing the fluid and configured to generate a selected color of the variable color radiation in response to a signal from the processor to illuminate a portion of the fluid discharged through the nozzle of the container with the selected color.

31. The system of claim 30, wherein the light system is configured to produce a rainbow effect on the discharged portion of the fluid.

32. The system of claim 30, wherein the light system changes the color of the discharged portion of the fluid in response to the processor.

33. The system of claim 30, wherein the container is an aerosol can.

34. The system of claim 30 wherein the at least one light source comprises a plurality of LEDs of different colors, of which at least one first color LED radiates at a first wavelength different from a second wavelength at which at least one second color LED radiates.

35. A method of illuminating a fluid not intended for human consumption, comprising:
disposing the fluid in a substantially transparent or translucent container;
providing a light system in operative connection with the container, the light system comprising a light source controllable by a processor for generating a variable color radiation; and
generating a selected color by the light system in response to a signal from the processor to illuminate the fluid.

36. The method of claim 35, wherein the light system illuminates a portion of the fluid being discharged from the container.

37. A system for illuminating a fluid not intended for human consumption, comprising:
a substantially transparent or translucent container for storing the fluid; and
a light system in operative connection with the container, the light system comprising a light source controllable by a processor for generating a variable color radiation; and configured to generate a selected color in response to a signal from the processor to illuminate the fluid.

38. The system of claim 37, wherein the light system illuminates a portion of the fluid being discharged from the container.

39. The system of claim 37 wherein the light source comprises a plurality of LEDs of different colors, of which at least one first color LED radiates at a first wavelength different from a second wavelength at which at least one second color LED radiates.

* * * * *